(12) United States Patent
Yazawa et al.

(10) Patent No.: US 9,714,449 B2
(45) Date of Patent: Jul. 25, 2017

(54) NUCLEIC ACID AMPLIFICATION METHOD

(71) Applicant: HITACHI HIGH-TECHNOLOGIES CORPORATION, Tokyo (JP)

(72) Inventors: Yoshiaki Yazawa, Tokyo (JP); Takahide Yokoi, Tokyo (JP); Chihiro Uematsu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 364 days.

(21) Appl. No.: 14/364,940

(22) PCT Filed: Nov. 22, 2012

(86) PCT No.: PCT/JP2012/080307
§ 371 (c)(1),
(2) Date: Jun. 12, 2014

(87) PCT Pub. No.: WO2013/088935
PCT Pub. Date: Jun. 20, 2013

(65) Prior Publication Data
US 2014/0342922 A1   Nov. 20, 2014

(30) Foreign Application Priority Data

Dec. 13, 2011 (JP) ................................ 2011-272117

(51) Int. Cl.
*C12Q 1/68* (2006.01)
(52) U.S. Cl.
CPC ......... *C12Q 1/6874* (2013.01); *C12Q 1/6844* (2013.01)
(58) Field of Classification Search
None
See application file for complete search history.

(56) References Cited

U.S. PATENT DOCUMENTS 5,470,724 A * 11/1995 Ahern ................. C07K 14/415
435/91.2
5,712,124 A   1/1998 Walker
(Continued)

FOREIGN PATENT DOCUMENTS

GB          2398383 A    8/2004
JP       2011-000058 A    1/2011
(Continued)

OTHER PUBLICATIONS

Japanese Office Action received in corresponding Japanese Application No. 2011-272117 dated Mar. 15, 2016.
(Continued)

*Primary Examiner* — Samuel Woolwine
(74) *Attorney, Agent, or Firm* — Mattingly & Malur, PC

(57) ABSTRACT

A nucleic acid amplification method includes ligating a double-stranded adapter (20) containing adapter DNA strands capable of forming a folded structure to a double-stranded DNA (1, 2) containing a target DNA sequence (1) to prepare a cyclic DNA template composed of double-stranded DNA containing a nick (5). A 3'-end elongation reaction is performed using a strand-displacement DNA polymerase from the nick (5) as an origin, thereby producing a concatemer (29) in which a plurality of the target DNA sequences (1) and the adapter DNA strands capable of forming the folded structure are linked in series as a single-stranded DNA. The concatemer (29) contains a plurality of the target DNA sequences (1) suitable for nucleotide sequence analysis and has a folded shape such that it takes the form of a ball due to its folded structure.

5 Claims, 13 Drawing Sheets
(1 of 13 Drawing Sheet(s) Filed in Color)

(56) References Cited

U.S. PATENT DOCUMENTS

| | | | |
|---|---|---|---|
| 6,235,502 B1 | 5/2001 | Weissman et al. | |
| 7,910,354 B2 | 3/2011 | Drmanac et al. | |
| 8,153,375 B2 | 4/2012 | Travers et al. | |
| 2002/0012930 A1* | 1/2002 | Rothberg | B01L 3/5027 435/5 |
| 2006/0035344 A1* | 2/2006 | Pachuk | A61K 48/00 435/91.1 |
| 2009/0080273 A1 | 3/2009 | Sohn | |
| 2009/0181861 A1* | 7/2009 | Li | C12Q 1/6869 506/16 |
| 2009/0233291 A1* | 9/2009 | Chen | C12Q 1/6809 435/6.11 |
| 2009/0270273 A1 | 10/2009 | Burns et al. | |
| 2009/0280538 A1 | 11/2009 | Patel et al. | |
| 2009/0298075 A1 | 12/2009 | Travers et al. | |
| 2010/0028953 A1* | 2/2010 | Koch | C12N 15/10 435/91.1 |
| 2010/0047773 A1* | 2/2010 | Koch | C12Q 1/6816 435/6.12 |
| 2011/0281768 A1 | 11/2011 | Travers et al. | |
| 2014/0329712 A1* | 11/2014 | Edwards | C12Q 1/6869 506/9 |
| 2014/0378318 A1* | 12/2014 | Brentano | C12Q 1/6855 506/2 |

FOREIGN PATENT DOCUMENTS

| | | |
|---|---|---|
| WO | 00/15779 A2 | 3/2000 |
| WO | 2006/084132 A2 | 8/2006 |
| WO | 2009-089384 A1 | 7/2009 |
| WO | 2009-120372 A2 | 10/2009 |
| WO | 2009/132028 A1 | 10/2009 |

OTHER PUBLICATIONS

Extended European Search Report received in corresponding European Application No. 12856949.8 dated May 28, 2015.

Shendure et al., "Next-generation DNA sequencing", Nature Biotechnology, 2008, pp. 1135-1145, vol. 26.

Metzker, "Sequencing technologies-the next generation", Nature Reviews Genetics, 2010, pp. 31-46, vol. 11.

European Communication Pursuant to Article 94(3) EPC received in corresponding European Application No. 12 856 949.8 dated Sep. 26, 2016.

* cited by examiner (a)

(b)

(c)

(a)

(b)

(c)

(a)

(b)

(c)

(a)

(b)

(c)

```
SEQUENCE LISTING

<160> NUMBER OF SEQ ID NOS: 8

<210> SEQ ID NO 1
<211> LENGTH: 40
<212> TYPE: DNA
<213> ORGANISM: Artificial
<220> FEATURE:
<223> OTHER INFORMATION: Synthetic DNA

<400> SEQUENCE: 1
gtacgggtct cacccgcgcc agggttttcc cagtcacgac                            40

<210> SEQ ID NO 2
<211> LENGTH: 38
<212> TYPE: DNA
<213> ORGANISM: Artificial
<220> FEATURE:
<223> OTHER INFORMATION: Synthetic DNA

<400> SEQUENCE: 2
cctaaggtct cgcccgtcac acaggaaaca gctatgac                              38

<210> SEQ ID NO 3
<211> LENGTH: 40
<212> TYPE: DNA
<213> ORGANISM: Artificial
<220> FEATURE:
<223> OTHER INFORMATION: Synthetic DNA

<400> SEQUENCE: 3
gtcgtgactg ggaaaaccct ggcgcgggtg agacccgtac                            40

<210> SEQ ID NO 4
<211> LENGTH: 38
<212> TYPE: DNA
<213> ORGANISM: Artificial
<220> FEATURE:
<223> OTHER INFORMATION: Synthetic DNA

<400> SEQUENCE: 4
gtcatagctg tttcctgtgt gacgggcgag accttagg                              38

<210> SEQ ID NO 5
<211> LENGTH: 28
<212> TYPE: DNA
<213> ORGANISM: Artificial
<220> FEATURE:
<223> OTHER INFORMATION: Synthetic DNA

<400> SEQUENCE: 5
cccgcgccag ggttttccca gtcacgac                                         28

<210> SEQ ID NO 6
<211> LENGTH: 24
<212> TYPE: DNA
<213> ORGANISM: Artificial
```

```
<220> FEATURE:
<223> OTHER INFORMATION: Synthetic DNA

<400> SEQUENCE: 6
gtcgtgactg ggaaaaccct ggcg                                            24

<210> SEQ ID NO 7
<211> LENGTH: 22
<212> TYPE: DNA
<213> ORGANISM: Artificial
<220> FEATURE:
<223> OTHER INFORMATION: Synthetic DNA

<400> SEQUENCE: 7
gtcatagctg tttcctgtgt ga                                              22

<210> SEQ ID NO 8
<211> LENGTH: 26
<212> TYPE: DNA
<213> ORGANISM: Artificial
<220> FEATURE:
<223> OTHER INFORMATION: Synthetic DNA

<400> SEQUENCE: 8
cccgtcacac aggaaacagc tatgac                                          26
```

NUCLEIC ACID AMPLIFICATION METHOD

BACKGROUND OF THE INVENTION

Field of the Invention

The present invention relates to a method and a kit for amplifying a target DNA sequence and producing concatemers. The present invention further relates to a method, a kit, and an apparatus for determining a nucleotide sequence using the thus produced concatemers.

Background Art

In recent years, a rapid and highly sensitive nucleotide sequencing method based on massively parallel nucleotide sequencing has been developed (Non-patent Document 1), and the widespread use of apparatuses involving such technology makes it possible to analyze the full genome of a plant, a fungus, an animal, a bacterium, or a virus within 1 week. The obtained nucleotide sequence information is now crucial in the fields of drug discovery, medicine, and agriculture. The range of the applications of genetic sequence information will undoubtedly further expand. Further improvement in throughput and accuracy will be required in the future. Moreover, it is also considered that fields such as the field of expression analysis requiring accurate quantitative performance will experience significant growth.

In massively parallel nucleotide sequencing, millions to billions of monoclonal DNA fragment clusters are disposed on a flow path substrate, and then the nucleotide sequences of DNA fragments of each cluster are read in parallel, thereby realizing a high throughput. The means employed for the production of many clusters and the disposition of the clusters on a flow path substrate are techniques such as (a) PCR that is performed with an end of template DNA immobilized on a flow path substrate, (b) immobilization of emulsion PCR (emPCR) products to solid beads, and (c) formation of DNA nanoballs by isothermal amplification using cyclic DNA.

PRIOR ART DOCUMENTS

Patent Documents

Patent Document 1: U.S. Pat. No. 7,910,354
Patent Document 2: JP Patent Publication No. 2011-509095 A (WO 2009/089384)
Patent Document 3: U.S. Pat. No. 5,712,124
Patent Document 4: U.S. Pat. No. 6,235,502
Patent Document 5: U.S. Patent Application Publication No. 2009/0270273
Patent Document 6: JP Patent Publication No. 2011-000058 A Non-Patent Documents Non-patent Document 1: J. Shendure and H. Ji, "Next-generation DNA sequencing", Nature Biotechnology, Vol. 26, pages 1135-1145, 2008
Non-patent Document 2: M. L. Metzker, "Sequencing technologies-the next generation", Nature Reviews Genetics, Vol. 11, pages 31-46, 2010

SUMMARY OF INVENTION

Problem to be Solved by the Invention

Massively parallel nucleotide sequencing has greatly contributed to improvement in analysis throughput and accuracy, but it takes much time and effort to dispose many clusters on a flow path substrate. This becomes an obstacle to improvements in throughput and accuracy. Technical development to further improve quantitative performance is required. Massively parallel nucleotide sequencing involves the disposition of many clusters, in which monoclonal DNA fragments are accumulated, on a flow path substrate and reading the sequences of each cluster in parallel. Several examples relating to a method for forming clusters on a flow path substrate are described in Non-patent Document 2. Representative cluster formation techniques (a) to (c) that have been proposed conventionally are considered as follows.

Technique (a) involves performing amplification on a flow path substrate and immobilizing monoclonal amplification products on site within a narrow range on such substrate. Hence, monoclonal clusters can be formed with relative ease. However, with this method, monoclonal DNA fragments serving as origins for cluster formation are randomly immobilized on a flow path substrate. Hence, highly dense disposition of clusters is difficult. Technique (b) involves immobilizing DNA fragments on solid beads by emulsion PCR (emPCR). One difficulty with this method is that it requires much time and effort to handle the emulsion and to screen out magnetic beads on which DNA fragments have not been immobilized. Technique (c) involves forming DNA nanoballs (DNB) by RCA (Rolling Circle Amplification) and then immobilizing them on a flow path substrate. Hence, highly dense clusters can be obtained with relatively little effort (e.g., Patent Documents 1 and 5).

A common problem with techniques (a), (b), and (c) is the presence of an amplification process that employs excessive amounts of primers with respect to template DNA. In PCR or RCA, the 3' end of a primer generally serves as an origin for nucleotide elongation in an amplification process (e.g., Patent Documents 1, 5, and 6). In massively parallel nucleotide sequencing, primers should be introduced into a solution in an amount sufficient for amplification using many DNA fragments as templates. The resulting partial and tentative binding of primers to each other results in unintended amplification products and deterioration in the quality of DNA libraries to be sequenced. Furthermore, primers for template amplification are designed so that they can hybridize to predetermined regions of DNA fragments to be amplified or predetermined regions of adapters having known sequences that have been added to DNA fragments to be amplified (e.g., Patent Document 6). However, nucleotide sequences within regions to be amplified are generally unknown, and sequence structures adjacent to such adapters are unpredictable. The initial amplification reaction (that is, a thermal denaturation process for DNA fragments to be amplified) is affected by the thermal stability of the nucleotide sequence structure. Hence, the hybridization efficiency of a primer varies each time a DNA fragment to be amplified having a different sequence is contained, and thus, the frequency distribution of the relevant DNA fragment after amplification differs from that of the template. This is an undesirable property for expression analysis, in which quantitative performance is particularly important.

As an example of a conventional nucleic acid amplification method, Patent Document 2 provides a consecutive amplification method, which uses cyclic DNA as a template and primers as origins. The object of the introduction of a nick therein is to stop an elongation reaction (starting from a nick) at another nick site generated at another position of cyclic DNA, but it is not to consecutively perform amplification of a target DNA sequence. According to Patent Document 4, a nick is similarly introduced into a cyclic DNA structure; however, no consecutive amplification is performed from a nick as an origin. An amplification method based on amplification starting from a nick is disclosed in Patent Document 3; however, no consecutive amplification method is provided therein.

As described above, in the case of massively parallel nucleotide sequencing, the time and effort required for the disposition of DNA libraries to be analyzed, which comprise many clusters, on a flow path substrate, are obstacles to further improvement in throughput and accuracy. Technical development for unification of amplification efficiencies among different templates is required in order to improve quantitative performance.

Therefore, an object of the present invention is to provide: a method and a means for convenient and rapid amplification of template DNAs having known or unknown sequences by reducing the time and effort required for amplification of template DNA and eliminating unintended amplification products that result from the binding of primers to each other in conventional amplification methods and frequency distribution fluctuations among DNAs to be amplified resulting from variation in primer hybridization efficiency; and a method and means for determining a nucleotide sequence using the same.

Means for Solving the Problem

As a result of intensive examination to address the above problems, the present inventors have succeeded in the production of a plurality of concatemers that are suitable for nucleotide sequence analysis by ligating adapters capable of forming a folded structure to template DNA, so as to prepare a cyclic DNA template, and then performing an elongation reaction that starts from a nick without the use of primers. The present inventors have further obtained the finding that each concatemer is folded as a result of its folded structure, allowing it to take the form of ball, which is suitable for nucleotide sequence analysis, and thus have completed the present invention.

The present invention includes the followings.

[1] A method for amplifying a nucleic acid, comprising the steps of:

(a) ligating a double-stranded adapter that contains adapter DNA strands capable of forming a folded structure to a double-stranded DNA that contains a target DNA sequence to prepare a cyclic DNA template composed of nick-containing double-stranded DNA; and (b) performing a 3' end elongation reaction from the nick as an origin using a strand-displacement DNA polymerase, thereby producing a concatemer in which a plurality of the target DNA sequences and the adapter DNA strands capable of forming the folded structure are linked in series as a single-stranded DNA, wherein the concatemer has a folded shape due to the folded structure.

[2] The method according to [1], wherein the double-stranded adapter has an adapter DNA strand that has a first DNA sequence, a second DNA sequence, and a third DNA sequence, wherein the first and the third DNA sequences are capable of forming a folded structure, and the adapter DNA strand and an adapter DNA strand complementary thereto are bound to form a double-strand.

[3] The method according to [2], wherein the double-stranded adapter has from the 5' end to the 3' end: an adapter DNA strand composed of the first DNA sequence, the second DNA sequence, and the third DNA sequence in this order; an adapter DNA strand composed of the first DNA sequence, the third DNA sequence, and the second DNA sequence in this order; or an adapter DNA strand composed of the second DNA sequence, the first DNA sequence, and the third DNA sequence in this order.

[4] The method according to [1], wherein the double-stranded adapter contains a first adapter DNA strand and a second adapter DNA strand complementary to the first adapter DNA strand, and the first adapter DNA strand and the second adapter DNA strand are bound to form a double-strand;

the first adapter DNA strand has, from the 5' end to the 3' end, a first DNA sequence, a second DNA sequence, and a third DNA sequence, and the first and the third DNA sequences are capable of forming a folded structure;

the second adapter DNA strand has, from the 5' end to the 3' end, a third complementary sequence complementary to the third DNA sequence, a second complementary sequence complementary to the second DNA sequence, and a first complementary sequence complementary to the first DNA sequence, and the first and the third complementary sequences are capable of forming a folded structure; and the method comprises the steps of:

(b1) generating a first nick at the 5' end of the first DNA sequence on the first adapter DNA strand, and generating a second nick at the 5' end of the third complementary sequence on the second adapter DNA strand, (b2) performing a 3' end elongation reaction from the first nick as an origin to the position of the second nick on the second adapter DNA strand using a strand-displacement DNA polymerase to generate an adapter DNA strand having the same sequence as that of the first adapter DNA strand and stop the elongation reaction, and thereby forming a folded structure by the adapter DNA strands, (b3) performing a 3' end elongation reaction of the adapter DNA strands to elongate a DNA sequence complementary to the target DNA sequence, and next generate an adapter DNA strand having the same sequence as that of the second adapter DNA strand, and thereby forming a folded structure by the adapter DNA strands, (b4) performing a 3' end elongation reaction of the adapter DNA strands to elongate the same DNA sequence as that of the target DNA sequence, and next generate an adapter DNA strand having the same sequence as that of the first adapter DNA strand, and thereby forming a folded structure by the adapter DNA strands, and (b5) repeating steps (b3) and (b4), such that a concatemer is produced, in which a plurality of the target DNA sequences, the first adapter DNA strands, the DNA sequences complementary to the target DNA sequences, and the second adapter DNA strands are linked in series.

[5] A method for determining a nucleotide sequence, comprising the steps of:

immobilizing one or a plurality of concatemers produced by the method according to any one of [1] to [4] on a flow path substrate;

binding a primer to a sequence other than sequences capable of forming a folded structure of the adapter DNA strands in each concatemer;

sequentially ligating a probe that contains a recognition site consisting of a plurality of nucleotides and is bound with a label corresponding to the nucleotide type of the recognition site to an end of the primer; and detecting the ligated probe based on the label to determine the nucleotide sequence of the target DNA sequence.

[5-2] The method according to [5], further comprising a step of producing one or a plurality of concatemers by the method according to any one of [1] to [4].

[5-3] The method according to [5], wherein the sequence other than sequences capable of forming a folded structure is a second sequence.

[6] A kit for performing the method of any one of [1] to [5], comprising a double-stranded adapter that contains a first adapter DNA strand and a second adapter DNA strand complementary to the first adapter DNA strand, in which the first adapter DNA strand and the second adapter DNA strand are bound to form a double-strand, wherein:

the first adapter DNA strand has a first DNA sequence, a second DNA sequence, and a third DNA sequence, and the first and the third DNA sequence are capable of forming a folded structure;

the second adapter DNA strand has a third complementary sequence complementary to the third DNA sequence, a second complementary sequence complementary to the second DNA sequence, and a first complementary sequence complementary to the first DNA sequence, and the first and the third complementary sequences are capable of forming a folded structure; and one of or both the first adapter DNA strand and the second adapter DNA strand have a sequence that contains a nick or is capable of generating a nick.

[7] The kit according to [6], wherein the nick is contained or generated at the 3' end or the 5' end of the second DNA sequence of the first adapter DNA strand, and/or the 3' end or the 5' end of the second complementary sequence of the second adapter DNA strand.

[8] The kit according to [6], wherein the nick is contained or generated at the 5' end of the first DNA sequence of the first adapter DNA strand and/or the 5' end of the third complementary sequence of the second adapter DNA strand.

[9] The kit according to any one of [6] to [8], wherein the first adapter DNA strand has, from the 5' end to the 3' end, the first DNA sequence, the second DNA sequence, and the third DNA sequence.

[9-2] The kit according to any one of [6] to [9], wherein the double-stranded adapter has a blunt end or a cohesive end.

[9-3] The kit according to any one of [6] to [9], wherein the sequence capable of generating a nick is a recognition site for a nicking enzyme.

[10] The kit according to any one of [6] to [9], further comprising a primer specifically binding to the second DNA sequence and/or a primer specifically binding to the second complementary sequence.

[11] An apparatus for determining a nucleotide sequence, comprising: a flow path substrate on which one or a plurality of concatemers produced by the method of any one of [1] to [4] are immobilized, a means for supplying a primer that binds to a sequence other than sequences capable of forming a folded structure in the adapter DNA strands contained in the concatemers, and a means for supplying a probe that contains a recognition site consisting of a plurality of nucleotides and is bound with a label corresponding to the nucleotide type of the recognition site; and a means for detecting the label.

[12] The apparatus according to [11], wherein the flow path substrate has pillar structures arranged periodically and the concatemers are each disposed on the top face of each of the pillar structures on the flow path substrate.

[13] The apparatus according to [12], wherein the cross-section diameter of each periodically arranged pillar structure and a single interval between any two such pillar structures are each 0.5 times to 3 times the maximum size of the outside of each concatemer when it is projected onto an arbitrary plane.

[14] The apparatus according to [12] or [13], wherein the side faces of the periodically arranged pillar structures and the surface of the flow path substrate are hydrophobic where the contact angle to water is 90 degrees or more.

[14-2] The apparatus according to any one of [11] to [14], further comprising a means for performing the method of any one of [1] to [4] to produce one or a plurality of concatemers.

This description includes part or all of the contents as disclosed in the description and/or drawings of Japanese Patent Application No. 2011-272117, which is a priority document of the present application.

Effect of the Invention

According to the present invention, a method and kit for amplifying a nucleic acid are provided. The method and kit make it possible not only to conveniently and efficiently perform nucleic acid amplification, but also to eliminate the generation of artifacts from conventionally used primers and to perform nucleic acid amplification while maintaining the abundance ratio of DNA molecules to be amplified. Thus the time and effort are saved, and the throughput and the accuracy are increased. Moreover, optimally-shaped concatemers that contain an optimal number of target DNA sequences for nucleotide sequencing may be produced by the method and kit for amplifying a nucleic acid. Therefore, the present invention is useful for conveniently determining a nucleotide sequence with a high throughput.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
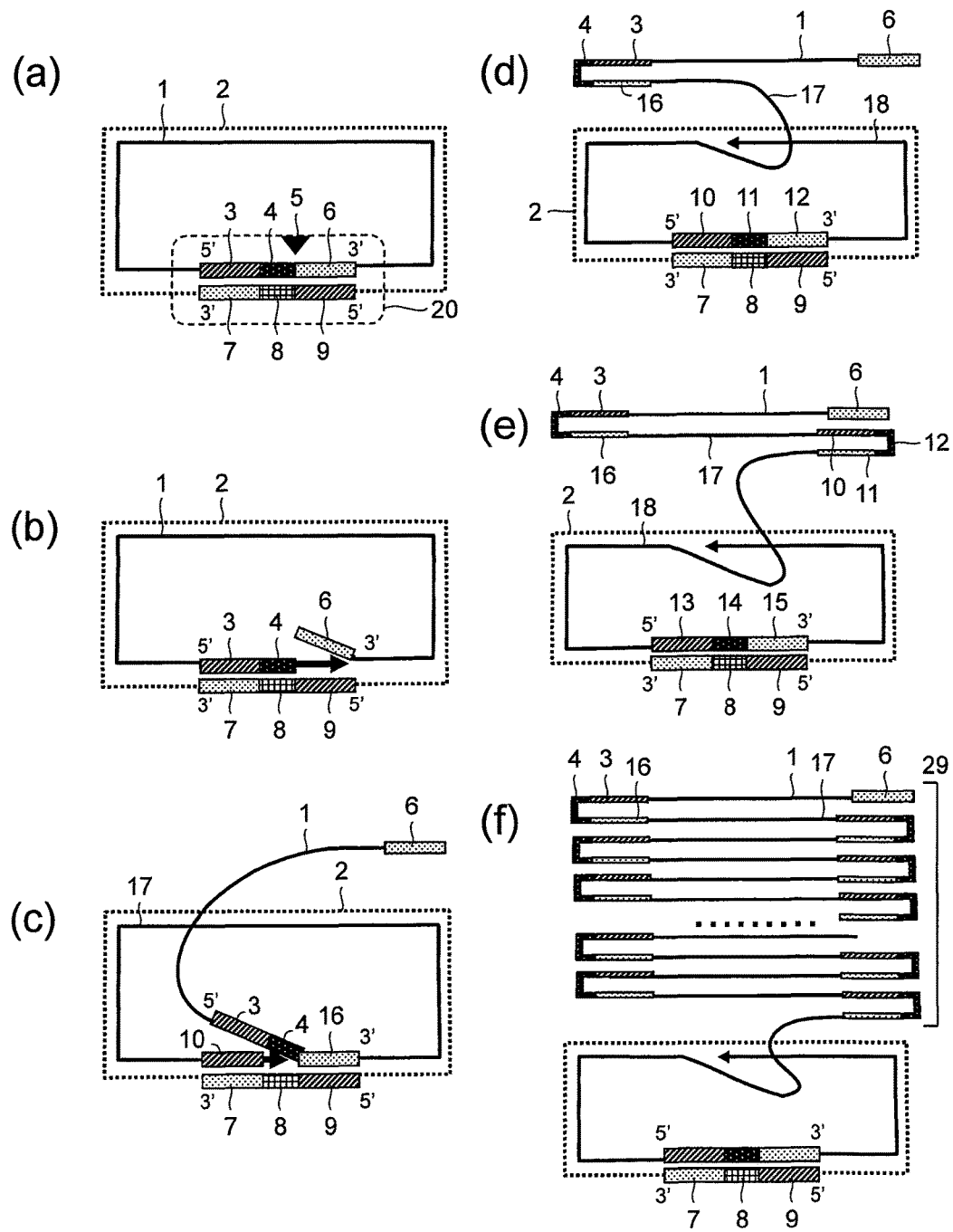
FIG. 1 shows an example of nucleic acid amplification reactions.

The present invention will be described in detail as follows.

The present invention provides a method and a means for amplifying a target DNA sequence. According to the present invention, a nick and an adapter capable of forming a folded structure are incorporated into a cyclic double-stranded template in order to obtain amplification products, the numbers and the shapes of which are appropriate for nucleotide sequencing that is performed subsequently. Accordingly, concatemers containing target DNA sequences, the number of which is appropriate for nucleotide sequencing, and having a shape appropriate for the same can be produced.

First, a double-stranded DNA containing a target DNA sequence is prepared. Double-stranded DNA containing a target DNA sequence is not particularly limited, as long as it is DNA containing a sequence to be amplified or sequenced. Examples thereof include genomic DNA, complementary DNA (cDNA), and synthesized DNA. The origin thereof is not particularly limited. Examples thereof that can be used herein include double-stranded DNA derived from arbitrary sources such as living bodies (e.g., cells, tissues, and liquids) and synthetic sources (e.g., DNA libraries such as a cDNA library). In the case of a source derived from a living body, the living body is not particularly limited. Examples of sources derived from arbitrary living bodies, which can be used herein, include vertebrates (e.g., mammals, birds, reptiles, fishes, and amphibians), invertebrates (e.g., insects, nematodes, and crustaceans), protozoa, plants, fungi, bacteria, and viruses.

Double-stranded DNA can be prepared by methods known in the art. For example, when double-stranded DNA is prepared from cells, cells can be lysed using protease such as Proteinase K, a chaotropic salt such as guanidine thiocyanate-guanidine hydrochloride, a surfactant such as Tween and SDS, or a commercially available cell lysis reagent, and then nucleic acid contained therein; that is, genomic DNA and RNA can be eluted. Genomic DNA may be fragmented by physical cleavage or cleavage with restriction enzymes. When cDNA is prepared, DNA among nucleic acids eluted by cell lysis can be degraded by a DNA-degrading enzyme (DNAse) to obtain a sample containing RNA alone as nucleic acid. Only mRNA may be captured using a DNA probe containing a polyT sequence, and then a reverse transcription reaction may be performed from mRNA using reverse transcriptase, so that cDNA can be synthesized. Alternatively, an amplification reaction may be performed using the above-prepared DNA or RNA, or a DNA library as a template, and thus double-stranded DNA can also be prepared. Kits for DNA preparation are commercially available from many manufacturers. Target double-stranded DNA can be conveniently purified.

Double-stranded DNA may contain a single type of DNA or a plurality of types of DNA. Specifically, double-stranded DNA may contain the same target DNA sequence, or different sequences. For example, double-stranded DNA can be used as DNA pools, cDNA libraries or the like. For example, in the present invention, a plurality of types of cDNA contained in cDNA libraries prepared from a plurality of types of mRNA can be uniformly amplified as double-stranded DNA.

Next, a double-stranded adapter may be ligated (linked) to the double-stranded DNA containing the target DNA sequence. According to the present invention, the term "double-stranded adapter" refers to DNA to be ligated to the double-stranded DNA containing the target DNA sequence for preparation of a cyclic DNA template. Such a double-stranded adapter may have any sequence with any length, as far as it contains adapter DNA strands capable of forming a folded structure. The double-stranded adapter has a double-stranded structure formed by binding of one adapter DNA strand to an adapter DNA strand complementary thereto.

According to the present invention, the term "folded structure" means a state in which, a sequence on an adapter DNA strand (single-stranded) and a sequence complementary thereto are bound, so that the single-stranded amplification product can be folded at the adapter DNA strand. Therefore, such an adapter DNA strand capable of forming a folded structure contains a sequence and a sequence complementary thereto. Preferably, for the formation of a "hairpin" or a "stem-loop" known in the art and the resulting formation of a folded structure, such an adapter DNA strand contains a sequence and a sequence complementary thereto (forming a stem moiety), and further contains another sequence (for forming a hairpin moiety or a loop moiety) not complementary to both sequences.

For example, when one of the adapter DNA strands in a double-stranded adapter has a first DNA sequence, a second DNA sequence, and a third DNA sequence, the first and the third DNA sequences are capable of forming a folded structure. Specifically, the first DNA sequence and the third DNA sequence are complementary to each other. Here, it is known in the art that a folded structure may be formed even when two sequences forming the structure are not completely (100%) complementary to each other. Therefore, the first DNA sequence and the third DNA sequence are complementary to each other to a degree such that both sequences can be bound. For example, at least 80%, preferably at least 90%, more preferably at least 95%, most preferably at least 98%, 99%, or 100% of nucleotides thereof are complementary to each other. Moreover, a sequence capable of forming a folded structure (e.g., first and third DNA sequences) may have a length appropriate for the formation of a folded structure, such as 10 to 100 nucleotides, and preferably 15 to 50 nucleotides. In addition, the first to the third DNA sequences can be placed in an adapter DNA strand without particular limitation and can be adequately placed by a person skilled in the art. For example, an adapter DNA strand may be composed of, from the 5' end to the 3' end: the first DNA sequence, the second DNA sequence, and the third DNA sequence, in this order; the first DNA sequence, the third DNA sequence, and the second DNA sequence, in this order; or the second DNA sequence, the first DNA sequence, and the third DNA sequence, in this order (for example, see FIG. 2). Preferably, an adapter DNA strand may be composed of, from the 5' end to the 3' end, the first DNA sequence, the second DNA sequence, and the third DNA sequence, in this order. The first and the third DNA sequences form a folded structure, while the second DNA sequence may be located between the first and the third DNA sequences, and thus a hairpin or a stem-loop structure may be formed.

In a preferred embodiment, a double-stranded adapter may contain a first adapter DNA strand and a second adapter DNA strand complementary to the first adapter DNA strand, in which the first adapter DNA strand and the second adapter DNA strand can be bound to form a double-strand, wherein:

the first adapter DNA strand has, from the 5' end to the 3' end, a first DNA sequence, a second DNA sequence, and a third DNA sequence, and the first and the third DNA sequences are capable of forming a folded structure;

the second adapter DNA strand has, from the 5' end to the 3' end, a third complementary sequence complementary to the third DNA sequence, a second complementary sequence complementary to the second DNA sequence, and a first complementary sequence complementary to the first DNA sequence, and the first and the third complementary sequences are capable of forming a folded structure.

Specific sequences and lengths of adapter DNA strands capable of forming a folded structure in a double-stranded adapter can be appropriately designed by a person skilled in the art depending on the length and type of a target DNA sequence to be amplified, the application of a concatemer after amplification, or the like. A double-stranded adapter may contain, in addition to the above-mentioned adapter DNA strands capable of forming a folded structure and another sequence (a hairpin moeity or a loop moeity) that is not complementary to both sequences, a restriction enzyme recognition sequence such that it can be ligated to a double-stranded DNA, for example. A double-stranded adapter can be prepared by known DNA synthesis methods or can be obtained from any commercial institutions that perform DNA synthesis on commission.

Methods for ligating a double-stranded adapter to a double-stranded DNA containing a target DNA sequence may not be particularly limited. For example, a double-stranded adapter may be prepared as one cassette, and then the cassette can be ligated to a double-stranded DNA to prepare a cyclic DNA template (e.g., see FIG. 3). Another method involves binding two sequences divided from a double-stranded adapter to both ends of a double-stranded DNA, and then linking the two sequences, so as to be able to form a cyclic DNA template (e.g., see FIG. 4). Ligation can be performed by methods known in the art, such as methods using restriction enzymes or ligase, for example. At this time, the junction between a double-stranded DNA and a double-stranded adapter may have a cohesive end or a blunt end.

The thus obtained cyclic DNA template may be designed to contain a nick (cleavage site). The term "nick" refers to a position at which the binding between nucleotides adjacent to each other in one strand of double-stranded DNA is cleaved. A nick can be set at any position of one of or both strands of a cyclic DNA template. For example, when a nick is set in one strand of a cyclic DNA template, a target DNA sequence or its complementary sequence may be amplified by a 3' end elongation (amplification) reaction described later, and thus a concatemer may be produced, in which a plurality of the target DNA sequences or their complementary sequences are linked in series. On the other hand, when nicks are set in both strands of a cyclic DNA template, both a target DNA sequence and its complementary sequence may be amplified by a 3' end elongation (amplification) reaction described later.

Preferably, a nick may be set in a double-stranded adapter. The position of a nick on a double-stranded adapter may not be particularly limited. A nick may be present at the 5' end or the 3' end of or any position on one strand of a double-stranded adapter. A nick may also be present at the 5' end of, the 3' end of, or any position on both strands of a double-stranded adapter (e.g., see FIG. 2). Methods for setting a nick may not be particularly limited. A nick can be set by methods known in the art. Examples thereof include: (i) a method that involves ligating a double-stranded adapter for which a nick has been set in advance to a double-stranded DNA; (ii) a method that involves dephosphorylating the 5' end of one adapter DNA strand of a double-stranded adapter; and (iii) a method that involves causing a nicking enzyme (e.g., N.BstNBI) that recognizes a recognition sequence to cleave a single strand of a double-strand to recognize the recognition sequence set in a double-stranded adapter, so as to generate a nick. For example, in a double-stranded adapter, a nick may be set in advance at any position or the 5' end of an adapter DNA strand, or a nucleotide sequence to be recognized by a nicking enzyme may be set in advance. Preferably, a nick may be contained in or generated at the 5' end of the first DNA sequence of a first adapter DNA strand and/or the 5' end of the third complementary sequence of a second adapter DNA strand.

A cyclic DNA template composed of nick-containing double-stranded DNA is prepared, and then a 3' end elongation reaction can be performed from the nick as an origin using a strand-displacement DNA polymerase. It has been known in the art that a new DNA strand may be synthesized as a result of "repair" performed by a strand-displacement DNA polymerase from the nick position (nick translation). According to the present invention, with the use of a strand-displacement DNA polymerase, a 3' end elongation reaction may be performed by rolling circle amplification (RCA) from a nick as an origin, so that a cyclic DNA template may be amplified.

The term "strand-displacement DNA polymerase" refers to a type of polymerase that is used for a 3' end elongation reaction (complementary strand synthesis), and that performs a 3' end elongation reaction while removing a double-stranded portion of template DNA. Polymerase that can be used in the present invention may not be particularly limited, as long as it has such a strand-displacement activity. Examples thereof include phi29 DNA polymerase, Bst DNA polymerase (Large fragment), Bca (exo-) DNA polymerase, Klenow fragment of *Escherichia coli* DNA polymerase I, Vent (Exo-) DNA polymerase (prepared by eliminating exonuclease activity from Vent DNA polymerase), Deep-Vent (Exo-) DNA polymerase (prepared by eliminating exonuclease activity from DeepVent DNA polymerase), and KOD DNA polymerase. Depending on the thus selected polymerase type, the reaction conditions for a 3' end elongation reaction may be adequately set. For example, when phi29 DNA polymerase is used, a reaction may be performed at an optimum temperature for the reaction, around 25° C. to 35° C. (about 30° C.). When BstDNA polymerase is used, a reaction may be desirably performed at around 60° C. to 65° C.

As a result of such 3' end elongation reaction, a concatemer may be produced, in which a plurality of target DNA sequences and adapter DNA strands capable of forming a folded structure are linked in series as a single-stranded DNA. When a nick is generated in one strand of a cyclic DNA template, such as one adapter DNA strand of a double-stranded adapter, a concatemer may be produced, in which a plurality of target DNA sequences and adapter DNA strands are linked in series as a single-stranded DNA (e.g., see FIG. 1). On the other hand, when nicks are generated in both strands of a cyclic DNA template, such as both adapter DNA strands of a double-stranded adapter, a concatemer may be produced, in which a plurality of target DNA sequences, one adapter DNA strand, DNA sequences complementary to the target DNA sequences, and other adapter DNA strand are linked in series (see FIG. 5). Such a concatemer contains target DNA sequences and DNA sequences complementary thereto. Through the binding of these sequences, the concatemer can be rigid as a cluster (collection/group) comprising the same sequences. In a specific embodiment, for example, the following steps can be performed:

(1) generating a first nick at the 5' end of the first DNA sequence on the first adapter DNA strand, and generating a second nick at the 5' end of the third complementary sequence on the second adapter DNA strand, (2) performing 3' end elongation reaction the first nick as an origin to the position of the second nick on the second adapter DNA strand using a strand-displacement DNA polymerase to generate an adapter DNA strand having the same sequence as that of the first adapter DNA strand, and stop the elongation reaction, and thereby forming a folded structure by the adapter DNA strands form, (3) performing a 3' end elongation reaction of the adapter DNA strands to elongate a DNA sequence complementary to the target DNA sequence, and next generate an adapter DNA strand having the same sequence as that of the second adapter DNA strand, and thereby forming a folded structure by the adapter DNA strands, (4) performing a 3' end elongation reaction of the adapter DNA strands to elongate the same DNA sequence as that of the target DNA sequence, and next generate an adapter DNA strand having the same sequence as that of the first adapter DNA strand, and thereby forming a folded structure by the adapter DNA strands, and (5) repeating steps (b3) and (b4), such that a concatemer is produced, in which a plurality of the target DNA sequences, the first adapter DNA strands, the DNA sequences complementary to the target DNA sequences, and the second adapter DNA strands are linked in series.

The above method makes it possible to perform nucleic acid amplification with uniform amplification efficiency without the need of any primer. The above-produced concatemer may have a form, in which a plurality of the target DNA sequences and the adapter DNA strands capable of forming a folded structure are linked in series, so that the folded structure may be formed and the concatemer may have a folded shape. Such a concatemer is a cluster (collection/group) containing a plurality of target DNA sequences, and thus it can be used for nucleotide sequencing, the detection of target DNA sequences, and others described later.

A concatemer that is produced by the nucleic acid amplification method of the present invention can be appropriately used for nucleotide sequencing methods, since it contains a plurality of target DNA sequences and has a folded shape (also referred to as "in the form of a ball") in which an existing space region is limited within a certain range. Therefore, the nucleic acid amplification method of the present invention can be performed as pretreatment for nucleotide sequencing.

In a method for determining a nucleotide sequence (nucleotide sequencing), one or a plurality of concatemers produced by the nucleic acid amplification method of the present invention may be immobilized on a substrate and preferably on a flow path substrate. A substrate or a flow path substrate mean a substrate on which a nucleotide sequencing reaction can be performed, which is known in the art. For example, solid substrates can be used but not particularly limited thereto, as long as they are generally used for procedures for nucleotide sequencing. Specific examples thereof include solid substrates that are insoluble in water and are not dissolved during thermal denaturation. Examples of materials therefor include: metals such as gold, silver, copper, aluminium, tungsten, molybdenum, chromium, platinum, titanium, and nickel; alloys such as stainless steel, hastelloy, inconel, monel, and duralumin; silicon; glass materials such as glass, quartz glass, fused quartz, synthetic quartz, alumina, sapphire, ceramics, forsterite, and photosensitive glass; plastics such as polyester resin, polystyrene, polyethylene resin, polypropylene resin, ABS resin (Acrylonitrile Butadiene Styrene resin), nylon, acryl resin, fluorine resin, polycarbonate resin, polyurethane resin, methylpentene resin, phenol resin, melamine resin, epoxy resin, and vinyl chloride resin; agarose, dextran, cellulose, polyvinyl alcohol, nitrocellulose, chitin, and chitosan. For detection of a reaction using a fluorescent label, a solid substrate made of a transparent material (e.g., glass and plastic) may be preferred. Moreover, the shape of such a substrate may not be particularly limited. Examples thereof include a flat plate, compartmentalized plane (e.g., a titer plate), films, tubes, and particles.

Methods for immobilizing a concatemer on a flow path substrate may not be particularly limited. Examples thereof include methods that involve performing immobilization by physical adsorption, covalent bonding, ionic bonding, or biological bonding (e.g., biotin-avidin binding or binding with streptavidin, and antigen-antibody binding).

Examples of methods for immobilizing a concatemer on a flow path substrate by physical adsorption include methods that involve binding a concatemer via electrostatic coupling on a flow path substrate, the surface of which has been treated with an amino silane molecule or cation (e.g., polylysine, polyallylamine, and polyethylenimine), with the use of the electric charge of the concatemer DNA.

A concatemer can be immobilized on a flow path substrate via covalent bonding, by, for example, introducing a functional group into the concatemer and introducing a functional group reactive to the functional group into the flow path substrate, so as to cause the two to react with each other. For example, an amino group may be introduced into a concatemer, an active ester group, an epoxy group, an aldehyde group, a carbodiimide group, an isothiocyanate group, or an isocyanate group may be introduced onto the surface of a flow path substrate, and thus a covalent bond can be formed. Moreover, a mercapto group may be introduced into a concatemer, an active ester group, a maleimide group, or a disulfide group may be introduced onto the surface of a flow path substrate. Examples of an active ester group include a p-nitrophenyl group, an N-hydroxysuccinimide group, a succinimide group, a phthalic imide group, and a 5-norbornene-2,3-dicarboximide group. An example of methods for introducing a functional group onto the surface of a flow path substrate is a method that involves treating the surface of a flow path substrate with a silane coupling agent having a desired functional group. Examples of a coupling agent that can be used herein include γ-aminopropyltriethoxysilane, N-β-(aminoethyl)-γ-aminopropyltrimethoxysilane, N-β-(aminoethyl)-β-aminopropylmethyldimethoxysilane, and γ-glycidoxypropyltrimethoxysilane. Another example of a method for introducing a functional group that serves as a binding site onto the surface of a flow path substrate is plasma treatment.

Next, in each concatemer, primers may be bound to sequences other than sequences capable of forming a folded structure in adapter DNA strands. Preferably, primers may be bound to a second DNA sequence in an adapter DNA strand, or a sequence that forms a hairpin moiety or a loop moiety. A primer can be designed based on a primer-binding region in an adapter DNA strand in view of the length and the melting temperature (Tm) using primer design procedures or a primer design program known in the art. The length of a primer ranges from, for example, 10 to 80 nucleotides, and preferably ranges from 12 to 30 nucleotides, and can be appropriately selected by a person skilled in the art. A concatemer contains a plurality of adapter DNA strands linked in series, so that primers can be bound to each adapter DNA strand.

To the ends of bound primers, a probe containing a recognition site consisting of a plurality of nucleotides and a label bound thereto corresponding to the nucleotide type of the recognition site may be ligated sequentially. The probe used herein may be similar to those used in conventional methods for determining a nucleotide sequence, and comprises a plurality of (any number of) nucleotides, such as about 2, 3, 4, 5, 6, 7, or 8 nucleotides. Such a plurality of nucleotides can be used in any combination of nucleotides. A plurality of types of probe containing recognition sites composed of various combinations of a plurality of nucleotides may be prepared and the probes may be sequentially used for ligation to the primer ends. Labels to be bound to probes may not be particular limited, as long as they are conventional labels in the art. Examples thereof include fluorescent labels (e.g., Cy3, Cy5, fluoresceinisothiocyanate (FITC), and tetramethyl rhodamineisothiocyanate (TRITC)), luminous semiconductor labels (e.g., zinc selenide (Zn—Se)), chemiluminescence labels (e.g., luciferin), enzyme labels (e.g., peroxidase, β-galactosidase, and alkaline phosphatase), and radioactive labels (e.g., tritium and iodine$^{125}$). In view of the ease for label detection, such label may be preferably a fluorescent label.

A probe can be ligated to the end of a primer only when it contains a recognition site corresponding to the nucleotide type of a target DNA sequence. Accordingly, through detection of a label, the nucleotide type of the recognition site of the ligated probe; that is, the nucleotide type of the target DNA sequence can be detected. A label can be detected according to the label type using methods and instruments known in the art. For example, a fluorescent label, a luminous semiconductor label, or a chemiluminescence label may be excited using an appropriate optical laser, and then can be detected using an optical system for counting the emitted light, fluorescence microscopy, a plate reader, or the like. In the case of an enzyme label, a substrate that develops color when degraded by the action of an enzyme may be added, and then the amount of the substrate degraded may be optically measured, and thus the label can be detected. In the case of a radioactive label, radiation quantity emitted by a radioactive label may be measured using a scintillation counter or the like. In the present invention, ligation of a primer to a probe may be preferably analyzed by counting the resulting luminescent spots using fluorescence.

By repeating the above procedures, the entire or a portion of the nucleotide sequence of a target DNA sequence can be determined.

The above-described method of the present invention can be conveniently performed through the use of a kit, while saving effort. The kit of the present invention may contain a double-stranded adapter which contains a first adapter DNA strand and a second adapter DNA strand complementary to the first adapter DNA strand, wherein the first adapter DNA strand and the second adapter DNA strand are bound to form a double-strand. Here, the first adapter DNA strand may have a first DNA sequence, a second DNA sequence, and a third DNA sequence, wherein the first and the third DNA sequence are capable of forming a folded structure, the second adapter DNA strand may have a third complementary sequence complementary to the third DNA sequence, a second complementary sequence complementary to the second DNA sequence, and a first complementary sequence complementary to the first DNA sequence, the first and the third complementary sequence are capable of forming a folded structure, and one of or both the first adapter DNA strand and the second adapter DNA strand may contain a sequence containing a nick or a sequence capable of generating a nick. An example of a sequence capable of generating a nick may be a recognition sequence for a nicking enzyme. The double-stranded adapter may have a blunt end or a cohesive end.

Furthermore, the kit of the present invention may further contain a primer specifically binding to the second DNA sequence, and/or a primer specifically binding to the second complementary sequence. In such a case, a method for determining a nucleotide sequence can be further performed conveniently.

Moreover, the present invention provides an apparatus for determining a nucleotide sequence. The apparatus for determining a nucleotide sequence according to the present invention comprises, for example, a flow path substrate on which one or a plurality of concatemers produced by the method of the present invention are immobilized, a means for supplying primers binding to sequences other than sequences capable of forming a folded structure in adapter DNA strands contained in the concatemers, and a means for supplying probes each containing a recognition site that consists of a plurality of nucleotides and a label bound thereto corresponding to the nucleotide type of the recognition site, and a means for detecting the label(s).

The apparatus for determining a nucleotide sequence may further comprise a means for performing the method according to the present invention, so as to produce one or a plurality of concatemers.

A flow path substrate to which concatemers have been immobilized may be a flow path substrate on which pillar structures are arranged periodically, wherein one concatemer is disposed on the top face of each pillar structure. Here, the term "pillar structure" refers to a structure that is provided vertically to the flow path substrate, which can be a fine pillar exemplified in Example 6, for example. The size of a pillar structure may be adequately set depending on the size of concatemers used herein, the signal level of labels used herein (e.g., fluorescence), and the like. Determining nucleotide sequence (nucleotide sequencing) requires concatemers to be immobilized with high surface density without overlapping each other on a flow path substrate by convenient procedures. Therefore, for example, the diameter of a pillar structure may be preferably set between 100 nm and 10 μm, and the height of a pillar structure may be preferably set between 100 nm and 10 μm. Furthermore, a single interval between any two such pillar structures (single interval between the center lines of these pillar structures adjacent to each other) may preferably range from 1 time to 10 times the diameter of each pillar structure.

Concatemers are composed of negatively charged DNA. By adjusting the range that is affected by the electric field resulting from the negative charge of concatemers and the pillar structure size, the concatemers can be immobilized on the top faces of pillar structures, at one concatemer per pillar structure, without overlapping each other because of their own repulsive force. For example, the cross-section diameter of each periodically arranged pillar structure and a single interval between any such pillar structures may be each 0.5 times to 3 times the maximum size of the outside of each concatemer when it is projected onto an arbitrary plane.

Moreover, in a flow path substrate, the top faces of periodically-arranged pillar structures may be preferably hydrophilic, and specifically preferably have surfaces such that the contact angle to water is 90 degrees or less. On the other hand, the sides of periodically arranged pillar structures and the surface of a flow path substrate may be preferably hydrophobic, and specifically preferably they have surfaces such that the contact angle to water is 90 degrees or more. To make these surfaces hydrophobic, for example, hydrophilicity and hydrophobicity (repellency) may be controlled under conditions of oxygen plasma treatment, or water repellency treatment may be performed for surfaces, or a flow path substrate may be produced with a water-repellent material. For example, the time for oxygen plasma surface treatment may be shortened, so that a state can be created wherein strong hydrophobicity is exhibited (such that the contact angle to water is 90° or more). Accordingly, immobilization of concatemers to portions other than the top faces of pillar structures can be avoided.

Examples of a means for detecting a label include a light irradiation means and a luminescence detection means, when fluorescent labels, luminous semiconductor labels, or chemiluminescence labels are measured. Such light irradiation means and a luminescence detection means can be selected and designed according to the label types to be used herein, excitation-luminescence wavelengths, and the like.

Moreover, the apparatus for determining a nucleotide sequence according to the present invention can also comprise a temperature control means, a means for supplying a washing solution, a washing unit, a means for draining a washing solution, and a means for recording the results of detecting labels, for example.

EXAMPLES

Specific examples of the embodiments of the present invention are described in detail with reference to drawings. However, it should be noted that these examples are given only as examples for realization of the present invention, and thus do not limit the present invention.

Example 1

In this example, a method for synthesizing concatemer molecules having a three-dimensional structure is an example of the reaction of nucleic acid amplification according to the present invention, and is explained with reference to FIG. 1.

A double-stranded adapter 20 having internal structures 3, 4, 6, 7, 8, and 9 is ligated to a double-stranded DNA fragment to be analyzed, comprising a target DNA fragment 1 and a DNA fragment 2 complementary thereto, using a ligation enzyme (FIG. 1(a)). The internal structures 3 and 6 and the internal structures 7 and 9 of the double-stranded adapter 20 have complementary sequences, which enable the formation of a folded structure within a solution. A sequence 4 may be any sequence that takes a single-stranded loop structure when the concatemer molecules 29 to be synthesized form a folded structure. The sequence 4 may be appropriate for designing a primer binding site in nucleotide sequence analysis described later on. A sequence 8 is complementary to the sequence 4. A nick 5 is generated at any position between the double-stranded adapter internal structures 4 and 6 of one of the adapter DNA strands in the double-stranded adapter 20. Here, the nick 5 can be generated at any position containing both ends of the double-stranded adapter as described later (FIG. 2). A ligation enzyme is made to act on the double-stranded adapter 20 and the double-stranded DNA fragments 1 and 2 to be analyzed, so that cyclic double-stranded DNA serving as a template for DNA amplification is generated.

Figure 2:
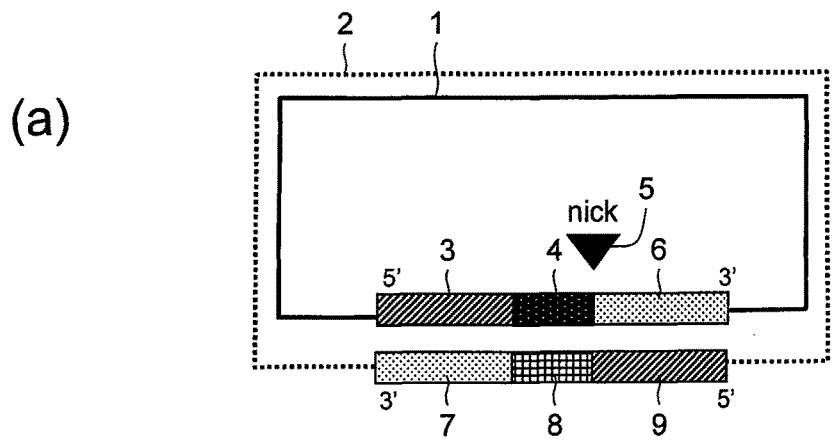
FIG. 2 shows configuration examples of a template for nucleic acid amplification reaction.
Figure 2:
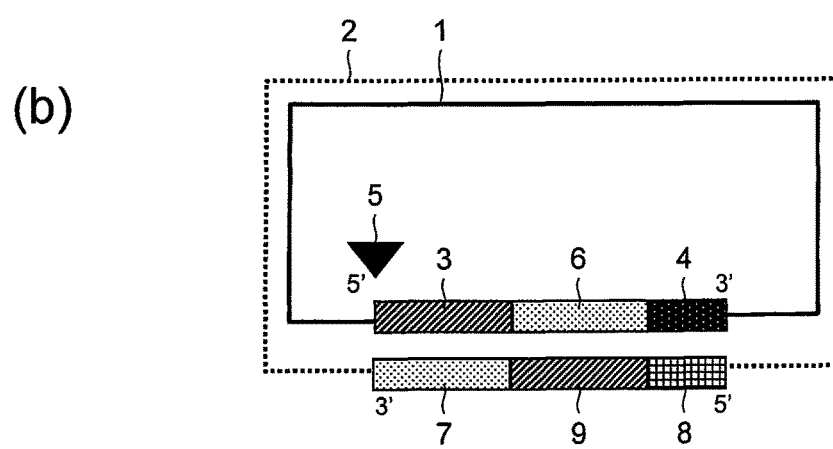
Figure 2:
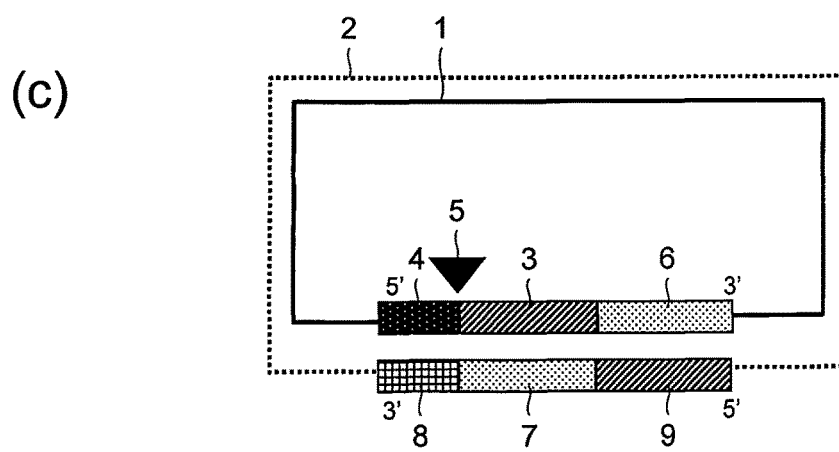

Strand-displacement DNA polymerase is caused to act on the template in which the nick 5 is generated at the position shown in FIG. 1 (a), and thus as shown in FIG. 1(b), DNA complementary strand synthesis takes place from the 3' end of the DNA sequence 4 with a DNA sequence 9 as a template, resulting in elongation. At this time, simultaneously with elongation of the 3' end of the sequence 4 by strand-displacement DNA polymerase, a sequence 16 is generated with 9 as a template, and the dissociation of a DNA sequence 6 that has originally bound to 9 proceeds. The 3' end is further elongated with the use of, as a template, a DNA fragment 2 composing a double-stranded DNA fragment to be analyzed, so as to generate a sequence 17 while dissociating the sequence of the target DNA fragment 1 that has bound to 2 before the reaction. This forms the second folded structures 10, 11, and 12, respectively, while dissociating 3, 4, and 16 (FIG. 1(c) (d)).

As shown in FIG. 1(d), a second elongation product 18 of the target DNA fragment is elongated while dissociation of 17, and thus folded structures 13, 14, and 15 are formed. 18 is dissociated by a similar elongation reaction (FIG. 1(e)). The reaction takes place continuously, so that the concatemers 29 are produced in which the target DNA fragments flanked by the folded structures are linked in series (FIG. 1(f). The reaction is continued, molecules that have produced concatemers form folded structures sequentially in their own nucleotide sequences, and thus the concatemer molecules form three-dimensional structures.

The position of a nick (serving as an origin for the synthesis of concatemer molecules) in one of the DNA strands in template DNA can be set at any position in a double-stranded adapter molecule. Folded structures in adapter structures may not be limited to the structures shown in FIG. 1. For example, structures shown in FIG. 2 can also be used herein. FIG. 2(a) shows template structures in which the adapter structures and the nick position shown in FIG. 1 are used. FIG. 2(b) shows a structure in which DNA sequences 3 and 6 capable of forming a folded structure are placed directly adjacent to each other, the sequence 4 is placed on the 3' end side of the sequence 6, and a nick is provided between the sequence 3 and the target DNA fragment 1. FIG. 2(c) shows a structure in which the DNA sequences 3 and 6 capable of forming a folded structure are placed directly adjacent to each other, the sequence 4 is placed on the 5' end side of the sequence 6, and a nick is provided between the sequence 3 and the sequence 4.

As a technique for causing a nick to be present at such a position, any one of the following techniques can be employed: (i) a method for synthesizing a double-stranded adapter in which a nick is present in advance; (ii) a method for dephosphorylating the 5' end of one of the DNA strands of a double-stranded adapter; and (iii) a method for generating a nick using a nicking enzyme that recognizes a specific nucleotide sequence set in a double-stranded adapter.

Figure 3:
FIG. 3 shows examples of a method for forming a cyclic DNA template for nucleic acid amplification reaction.
Figure 3:
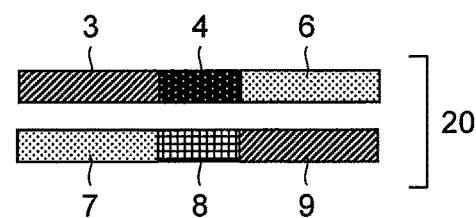
Figure 3:
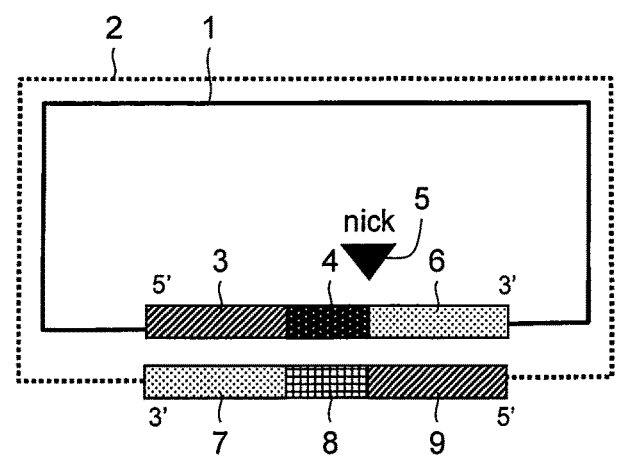
Figure 4:
FIG. 4 shows examples of a method for forming a cyclic DNA template for nucleic acid amplification reaction.
Figure 4:
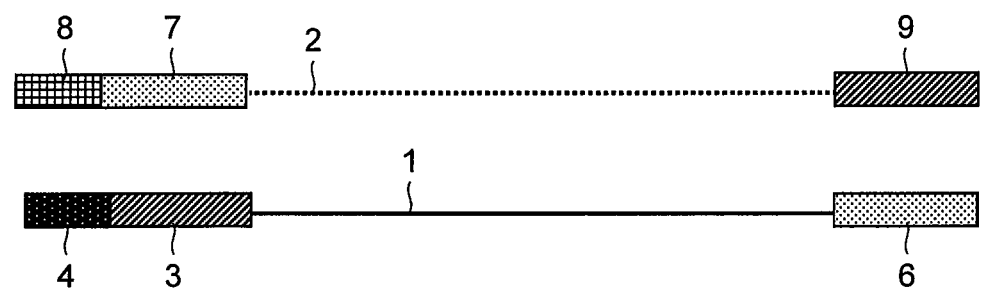
Figure 4:
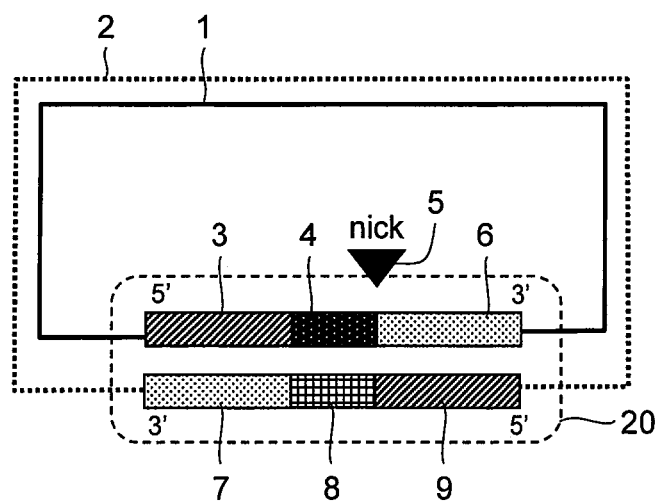

Next, two examples of a method for forming a cyclic template from double-stranded DNA fragments 1 and 2 to be analyzed, and the double-stranded adapter 20 are as explained as follows. The first example is shown in FIG. 3. Materials to be used herein are: double-stranded DNA fragments 1 and 2 (to be analyzed) prepared by the physical cleavage or the cleavage with a restriction enzyme of genomic DNA or the double-stranded DNA fragments 1 and 2 to be analyzed obtained through a DNA amplification method such as PCR (FIG. 3(a)); and the double-stranded adapter 20 that has a complementary DNA sequence in at least one of the DNA strands, which enables it to form a folded structure (FIG. 3(b)). These molecules are each linked using a ligation enzyme, so that cyclic double-stranded DNA molecules are synthesized (FIG. 3(c)). As the junction between the double-stranded DNA fragment 1 and 2 to be analyzed, and the double-stranded adapter 20, a structure having a generally-complementary cohesive nucleotide end is used. Linkage between DNA molecules having a blunt-end structure may also be applicable. The second example is shown in FIG. 4. A double-stranded adapter sequence is linked to each of both ends of 1 molecule of the double-stranded DNA fragments 1 and 2 to be analyzed (FIG. 4(a); and FIG. 4(b)), and then the two adapter sequences are bound, so that a cyclic double-stranded DNA molecule (FIG. 4(c)) can be synthesized. In this synthesis method, at the time (FIG. 4(b)) of ligation to the double-stranded DNA fragments to be analyzed (1 and 2 in FIG. 4), the sequences (3, 4, 6, 7, 8 and 9 in FIG. 4) among the double-stranded adapter may lack the ability to form a folded structure with complementary DNA sequences. However, at the stage of the formation of a cyclic double-stranded DNA molecule, the construction of a folded structure with complementary sequences within a single molecule can be expected in the resulting adapter region.

Example 2

In this example, a method for synthesizing concatemer molecules having a three-dimensional structure; that is, an example of the reaction of nucleic acid amplification according to the present invention is explained with reference to FIG. 5.

A double-stranded adapter 21 having internal structures 103, 104, 106, 107, 108, and 109 is ligated to double-stranded DNA fragments 101 and 102 (to be analyzed) comprising a target DNA fragment 101 and a DNA fragment 102 complementary thereto using a ligation enzyme (FIG. 5(a)). The internal structures 103 and 106, and 107 and 109 of the double-stranded adapter 21 have complementary sequences, making it possible to form a folded structure in a solution. A sequence 104 may be any sequence that takes a single-stranded loop structure when the synthesized concatemer molecules 129 form a folded structure. The sequence 104 can be used as a primer binding site in nucleotide sequence analysis described later on. In another example, a primer binding site can be set in any one of or across some of the internal structures 103, 104 and 106 of an adapter. A sequence 108 is complementary to the sequence 104. Here, a first nick 105 is generated between the target DNA fragment 101 and the adapter internal structure 103, and a second nick 155 is generated between a DNA fragment 102 complementary to the target DNA fragment 101 and the adapter internal structure 109. An elongation reaction can take place from the nick 105 or 155 as an origin. Concatemers of interest can be produced in both cases, however, a case of elongation with 105 as an origin is explained.

Strand-displacement DNA polymerase is caused to act on the template (FIG. 5(a)), and thus, as shown in FIG. 5(b), the 3' end of the target DNA fragment 101 is elongated with a DNA sequence 107 and then a DNA sequence 108 as templates, so as to generate 110 and 111. The dissociation of the DNA sequences 103, 104, and 106 that have originally bound to 107, 108, and 109 proceeds and the elongation stops at the position of the nick 155. When 110, 111, and 112 are dissociated from 107, 108, and 109 because of thermal fluctuation, 110, 111, and 112 form a folded structure due to the sequence complementarity of 110 and 112 (FIG. 5(c)). The 5' end of 109 is dephosphorylated and separated from the 3' end of 102 due to the presence of the nick 155 (FIG. 5(c)). The 3' end of 112 in the folded structure is elongated while using 101 as a template and dissociating 102, and thus a sequence 116 having a sequence complementary to the target DNA fragment 101 is generated. Subsequently, 106, 104, and 103 are used as templates to generate 113, 114, and 115 (FIG. 5(d)). 113, 114, and 115 are dissociated from 106, 104, and 103 due to thermal fluctuation, so as to form a folded structure based on the sequence complementarity of 113 and 115. The 3' end of 113 is elongated while using 116 as a template and dissociating 101 (FIG. 5(e)). A sequence 117 same as that of the target DNA fragment 101 is generated by an elongation reaction, and then 118, 119, and 120 are generated with 112, 111, and 110 as templates. In a manner similar to the above, a folded structure is formed because of thermal fluctuation and the sequence complementarity of 118 and 120. The 3' end of 120 is elongated with 101 as a template (FIG. 5(f)). The 3' end of 120 is elongated with 101 as a template while generating 121, and then 122, 123, and 124 are generated with 106, 104, and 103 as templates (FIG. 5(g)). By repeating these steps, a concatemer 129 is produced (FIG. 5(h)), in which the target DNA fragment and its complementary DNA fragment are alternatively repeated.

Example 3

Figure 5:
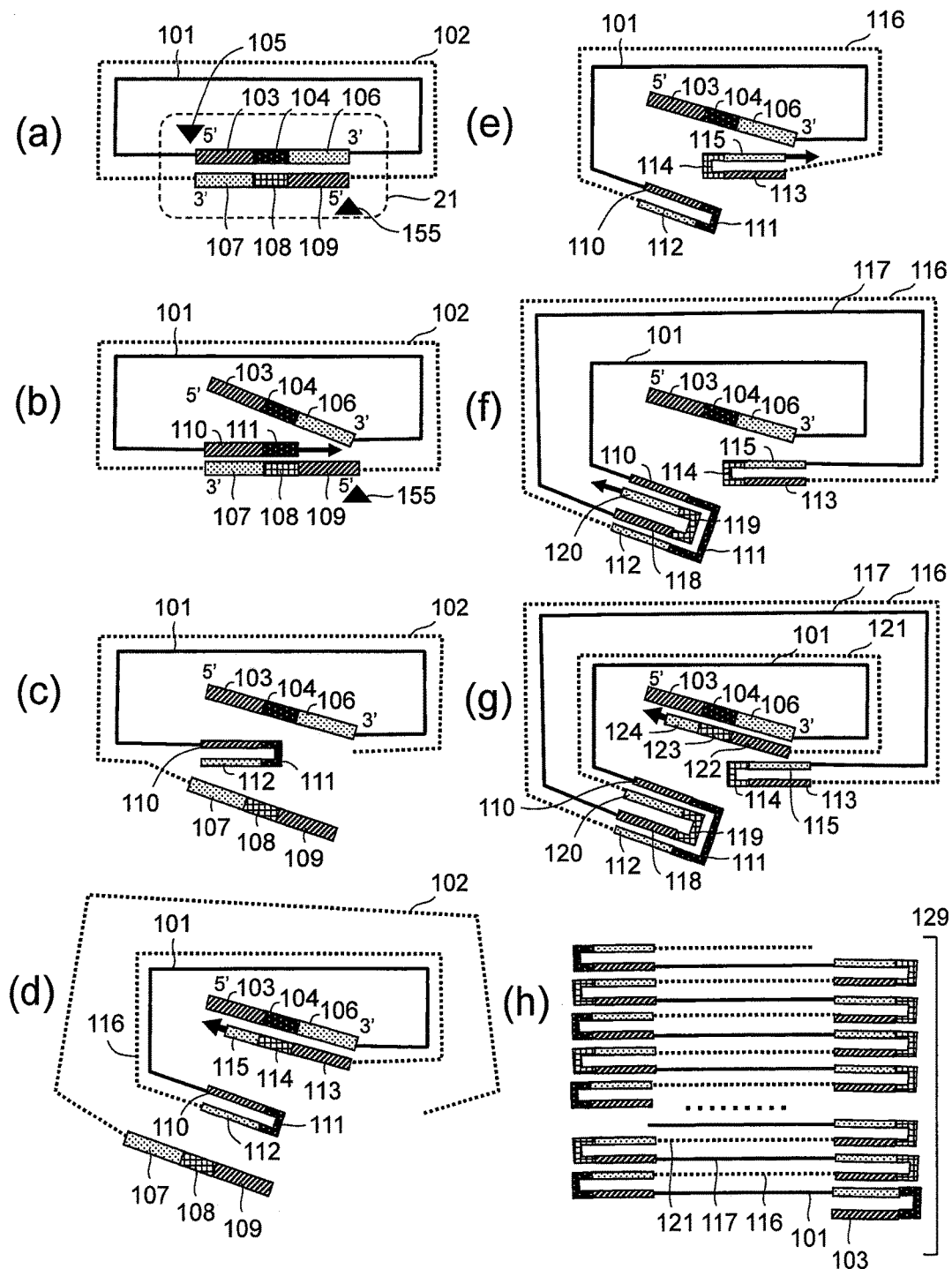
FIG. 5 shows another example of nucleic acid amplification reactions.
Figure 6:
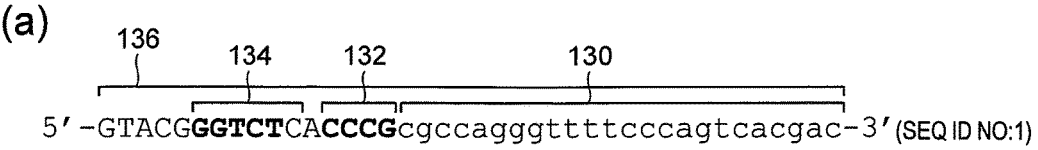
FIG. 6 shows examples of the sequence of a cyclic DNA template for nucleic acid amplification reaction.
Figure 6:
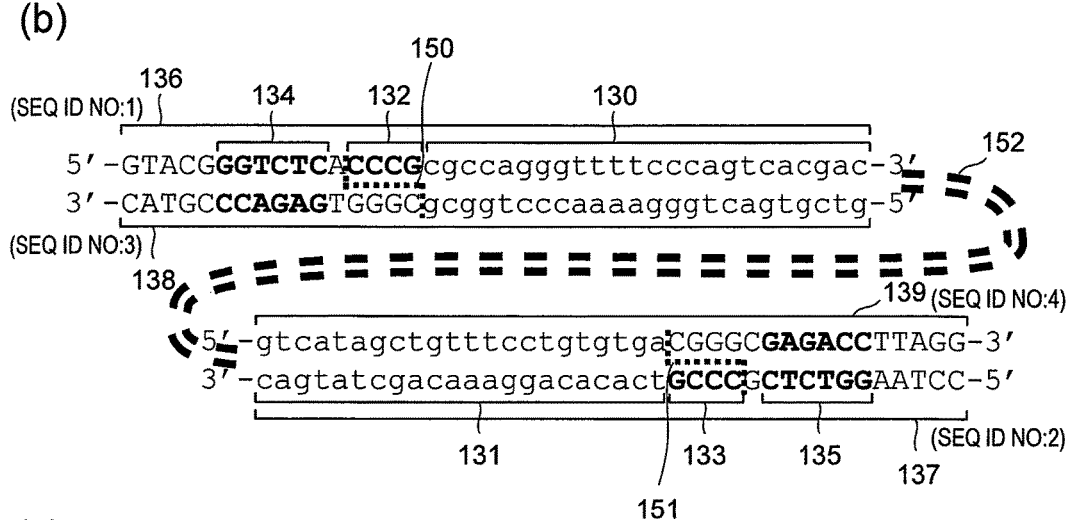
Figure 6:
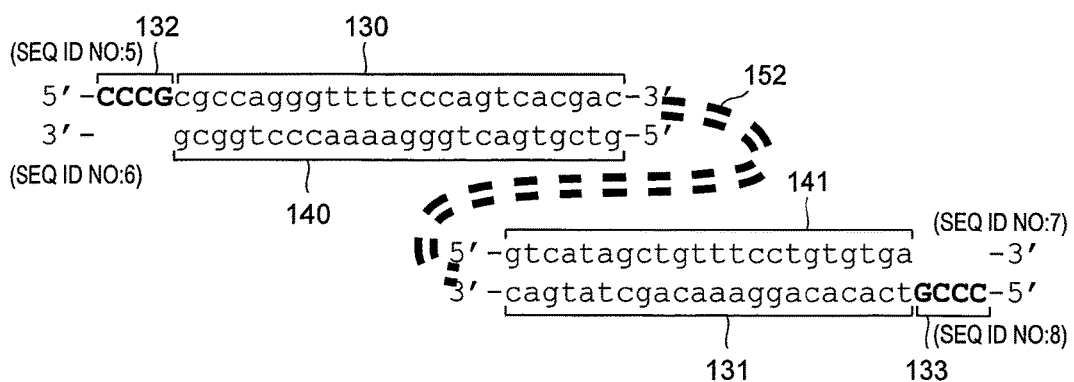
Figure 7:
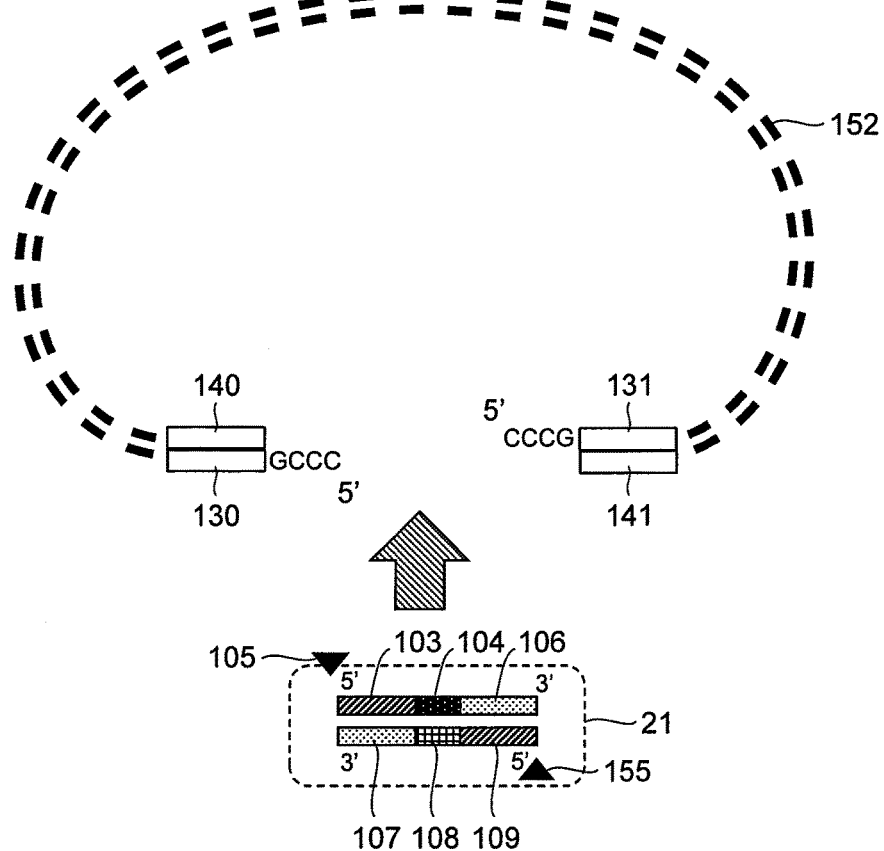
FIG. 7 shows examples of the formation of a cyclic DNA template for nucleic acid amplification reaction.
Figure 7:
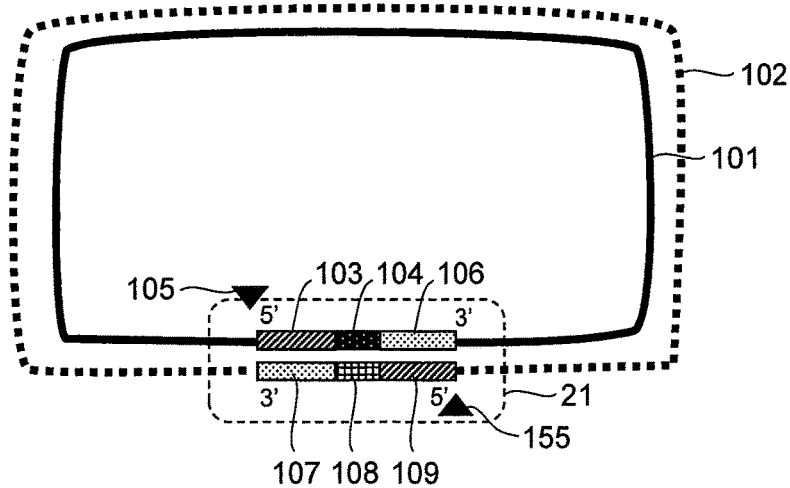

In this example, a method for producing concatemer molecules to be subjected to massively parallel nucleotide sequencing is exemplified with reference to FIGS. 5, 6, and 7.

A double-stranded DNA fragment to be analyzed is shown in 152 of FIG. 6(b). As 152, a partial fragment of pUC19 plasmid DNA which has been amplified by PCR can be used as an example of the double-stranded DNA fragment to be analyzed. The partial fragment of pUC19 plasmid can be amplified by a PCR method using a M13 forward primer sequence 130 (universal primer, as shown in FIG. 6(a)), a primer (M13_f01_BsaI) 136 (SEQ ID NO: 1) containing a recognition sequence 134 for a restriction enzyme Bsa I, a M13 reverse primer sequence 131, a primer (M13_f02_BsaI) 137 (SEQ ID NO: 2) containing a recognition sequence 135 for a restriction enzyme Bsa I, and pUC19 plasmid DNA as a template. Complementary sequences 138 and 139 (SEQ ID NOS: 3 and 4) are also generated (FIG. 6 (b)). The thus obtained amplification DNA product is cleaved at 150 and 151 with the restriction enzyme Bsa I (NEB), so that a double-stranded DNA fragment (to be analyzed) having cohesive ends 132 and 133, primer recognition sites 130 and 131, and DNA sequences 140 and 141 complementary thereto, is synthesized (FIG. 6(c)).

A double-stranded adapter 21 having a DNA sequence complementary to the cohesive end structure of a double-stranded DNA fragment (to be analyzed) 152 was chemically synthesized by dephosphorylating the 5' end of each DNA strand. The resultant was mixed with the previously synthesized double-stranded DNA fragment to be analyzed 152 (FIG. 7(a)), and then a cyclic double-stranded DNA molecule was synthesized by a ligation reaction with T4

DNA ligase (Invitrogen) (FIG. 7(b)). The cyclic double-stranded DNA molecule obtained in this step has one nick on each DNA strand as shown in FIG. 7, wherein the position at which each nick is present is at the 5' end position of the double-stranded adapter. The structure of FIG. 7(a) corresponding to that of FIG. 5(a) is shown in FIG. 7(b). Single-stranded DNA composing the double-stranded DNA fragment 152 containing the target DNA fragment 101 contains the target DNA fragment 101, a forward primer for PCR, a reverse primer for PCR, and a cohesive end-forming sequence. These sequences together correspond to the sequences of FIG. 7(b).

The thus synthesized cyclic double-stranded DNA molecule as a material, phi29 DNA Polymerase (NEB) as a strand-displacement DNA polymerase, and a dNTP solution as a reaction substrate are added, and then a nucleic acid amplification reaction is performed by the procedures of FIG. 5. In this step, the 3' end structure contributing as a starting point of a DNA elongation reaction is present only at the nick 105 or 155 in the cyclic double-stranded DNA molecules 101 and 102. An elongation reaction is initiated from a DNA molecule forming a cyclic double-stranded DNA molecule (FIG. 5(b)). A DNA elongation reaction with a complementary strand as a template stops at the position of the nick 155 that is present at the end part of the adapter sequence 109 of a complementary strand DNA molecule. Due to the presence of sequences 110 and 112 (of an adapter sequence newly generated by an elongation reaction) capable of forming a folded structure, the 3' end sequence forms a folded structure with respect to its own DNA molecule (FIG. 5(c)). After folding, with self (its own)-target DNA fragment 101 as a template sequence, the DNA elongation reaction is continued. At the stage where the self-target DNA fragment is used as a template to its end (FIG. 5(d)), the target DNA sequence to be used as a template is interrupted. However, because of the folded structure of the adapter sequences 113 and 115 that are present in the synthesized terminal sequence region, a fold is formed at each terminal sequence portion, and thus the DNA elongation reaction is continued with the self-DNA molecule as a template. In this step, an elongation reaction with the self-DNA molecule as a template and the folding of the terminal sequence at the terminal position consecutively take place, so that the concatemer molecules 129 containing the target DNA fragment repeated therein is synthesized (FIG. 5(h)). Because of the presence of the folded structure repeated in the concatemer molecule 129, a three-dimensional structure comprising the concatemer molecule is formed.

Figure 8:
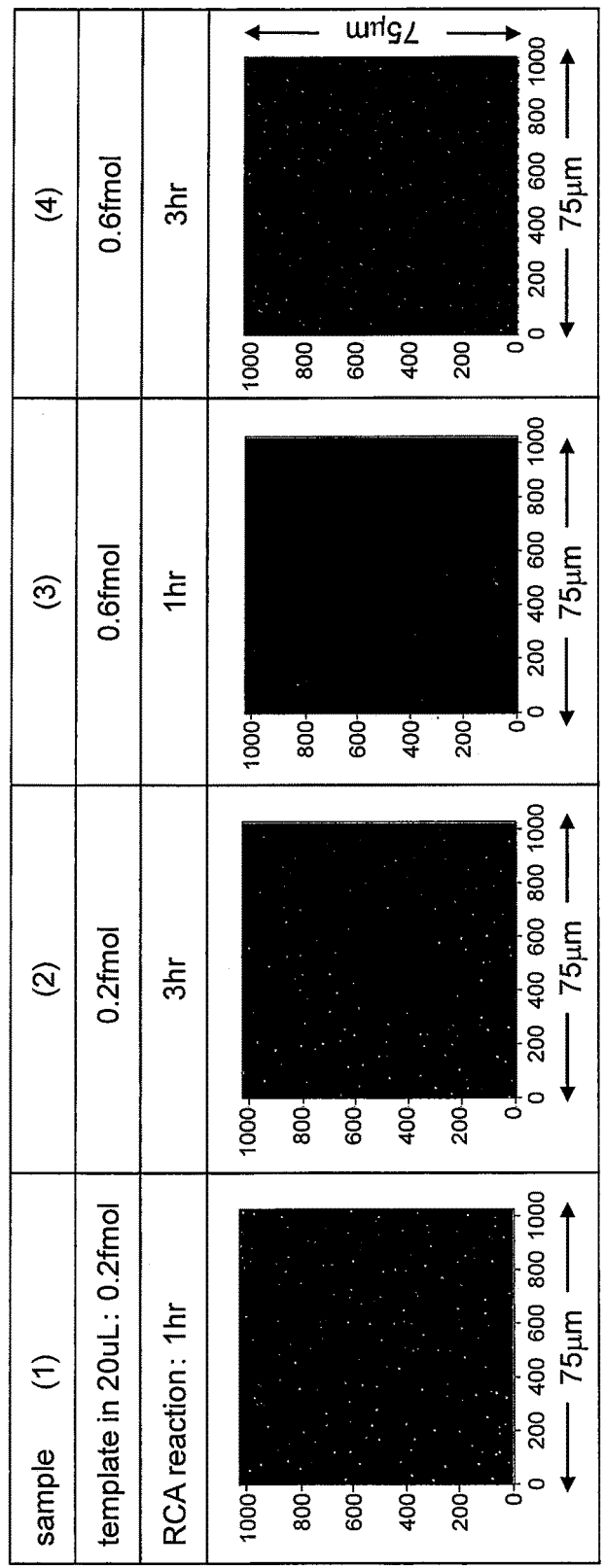
FIG. 8 shows the results of nucleic acid amplification reactions.

FIG. 8 shows the results of the production of concatemers by the above procedures. A cyclic double-stranded DNA molecule having the structure shown in FIG. 5(a) and comprising the sequences shown in FIG. 6(c) and an adapter was used as a template. Reaction conditions were as follows: template concentrations were 0.2 fmol and 0.6 fmol; and rolling circle amplification (RCA) was performed for 1 hour (1 hr) and 3 hours (3 hr). Observation was performed using PicoGreen (Invitrogen) for detection of double-stranded DNA. Luminescent spots shown in FIG. 8 each corresponds to one concatemer folded in the form of a ball due to the folded structure; meaning, clustered. Shown in this figure is the relationship between template concentration and reaction time, being: the higher the template concentration and the longer the reaction time, the higher the number of concatemers (e.g., sample (4) in FIG. 8).

Example 4

Figure 9:
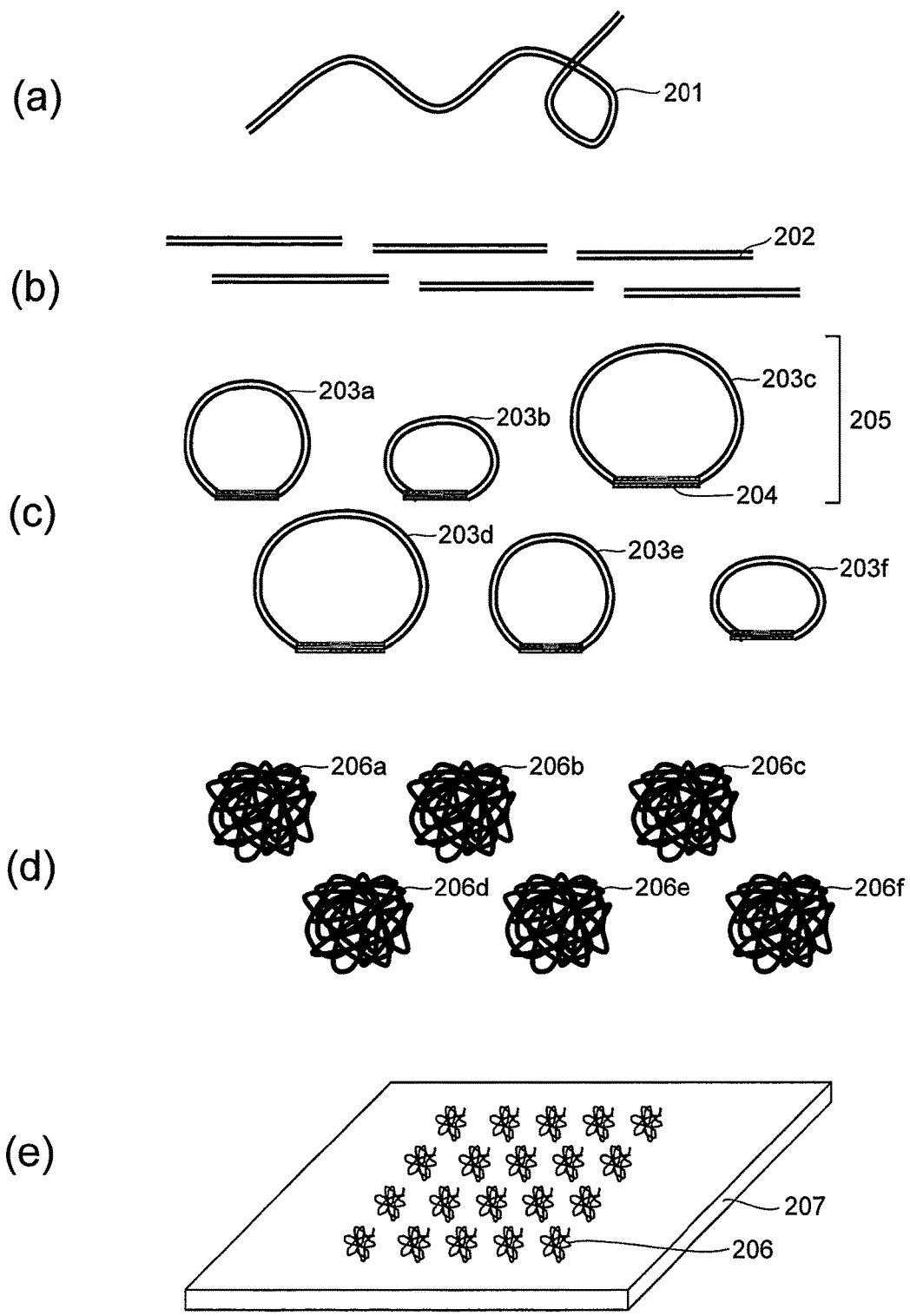
FIG. 9 shows an example of applying nucleic acid amplification reactions for nucleotide sequencing.

In the present invention, template DNA to be used for the production of concatemers can be subjected to sequencing. Template DNA can be collected from any cells, tissues, or organisms and prepared by any method used in the art. An example of this procedure is described with reference to FIG. 9.

For example, when genomic DNA 201 (FIG. 9(a)) is subjected to analysis, collected genomic DNA 201 is fragmented 202 to several hundred by (FIG. 9(b)). Terminal repair, "A" nucleotide addition, and ligation of double-stranded adapter DNA 204 are performed, and then fragments with nucleotide lengths that are out of the specification are removed. A template DNA 205 library containing target DNA sequences 203a-f and the adapter sequence 204 is generated (FIG. 9(c)). Amplification is performed with 205 as a template, and then three-dimensionally folded DNA-nanoball-shaped concatemers 206a-f are obtained. 206a-f are immobilized on a flow path substrate 207 and then subjected to sequence analysis.

Example 5

Figure 10:
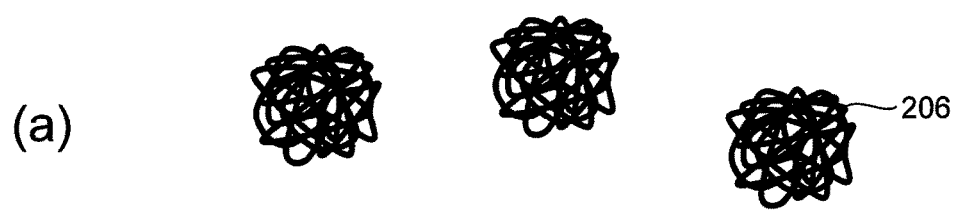
FIG. 10 shows an example of a method for immobilizing products from nucleic acid amplification reaction on a substrate of an apparatus for determining a nucleotide sequence.
Figure 10:
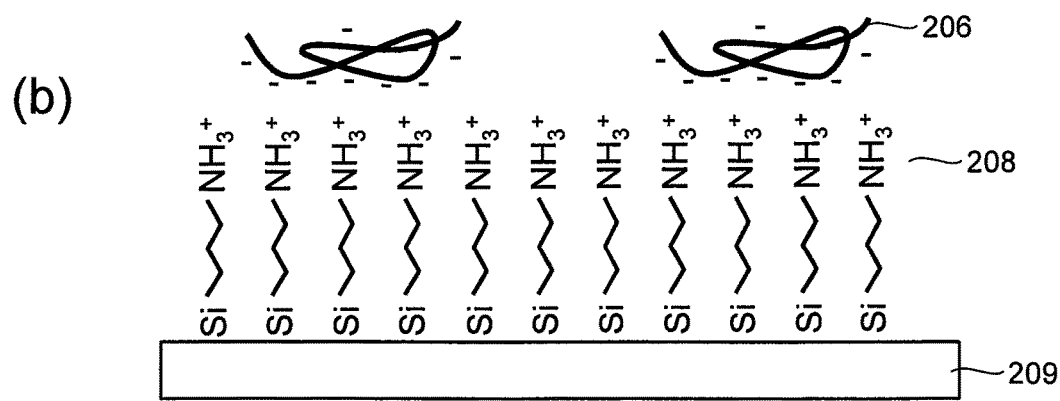
Figure 10:
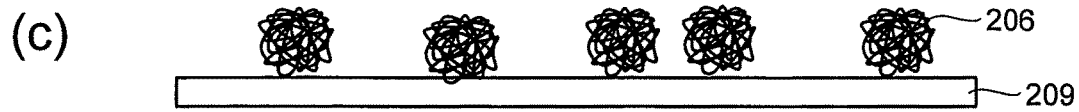

In this example, a method for immobilizing concatemer molecules 206 to be subjected to massively parallel nucleotide sequencing on a flow cell substrate 209 is exemplified in FIG. 10.

As is clarified in U.S. Patent Application Publication No. 2009/0270273 (Patent Document 5), concatemers 206 comprising DNA molecules are negatively charged, the surface of the flow cell substrate 209 made of glass is modified with an aminosilane molecule, the concatemers 206 are electrostatically bound to amino groups 208 on the surface of the substrate 209 (FIGS. 10(b) and (c)). Thus, the concatemers can be immobilized on the substrate.

Example 6

Figure 11:
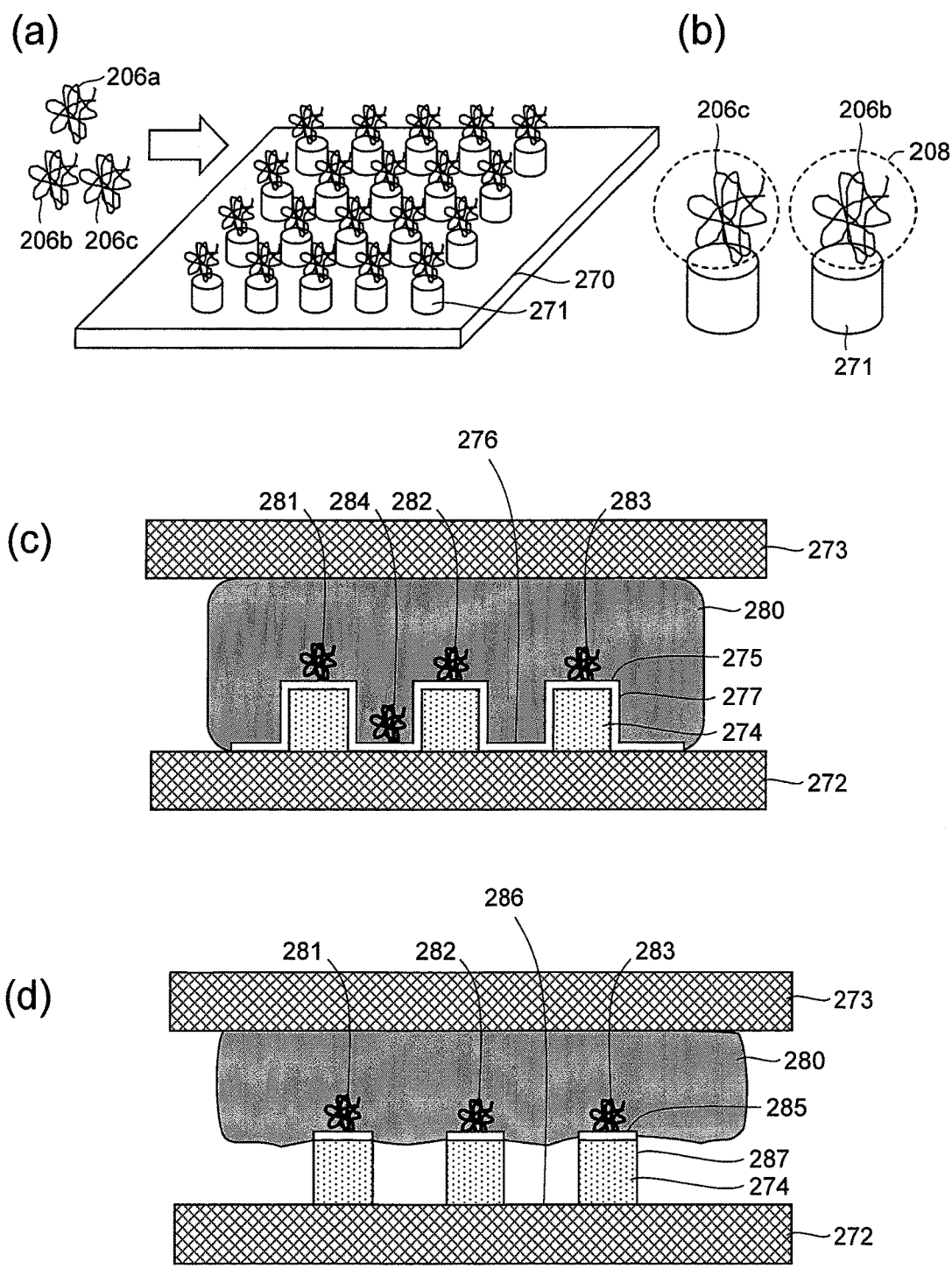
FIG. 11 shows another example of a method for immobilizing products from a nucleic acid amplification reaction on a substrate of an apparatus for determining a nucleotide sequence.

In this example, a method for immobilizing the concatemer molecules 206 (produced by procedures based on the present invention) to be subjected to massively parallel nucleotide sequencing on a flow cell substrate 270 is exemplified. This is explained with reference to FIG. 11, as follows.

Fine pillars 271 are formed on the inner faces of the flow cells of the flow cell substrate 270, which are made of glass. Concatemers 206a-c are immobilized on the top faces of the fine pillars 271. Here, the diameter of each fine pillar is desirably set ranging from 100 nm to 10 µm. A single interval between any two such fine pillars (single interval between the center lines of these pillar structures adjacent to each other) is desirably set ranging from 1 time to 10 times the diameter of each fine pillar. The height of each fine pillar is desirably set at a value between 100 nm and 10 µm. Sequence analysis requires that concatemers are immobilized with high surface density without overlapping each other on flow cells by convenient procedures. The concatemers 206 composed of negatively-charged DNA fragments. Hence, as shown in FIG. 11(b), concatemers are each disposed on the top face of one fine pillar due to their own repulsive force without overlapping with each other, when an area affected by the electric field resulting from the negative charge of each concatemer is designated as 208.

Figure 12:
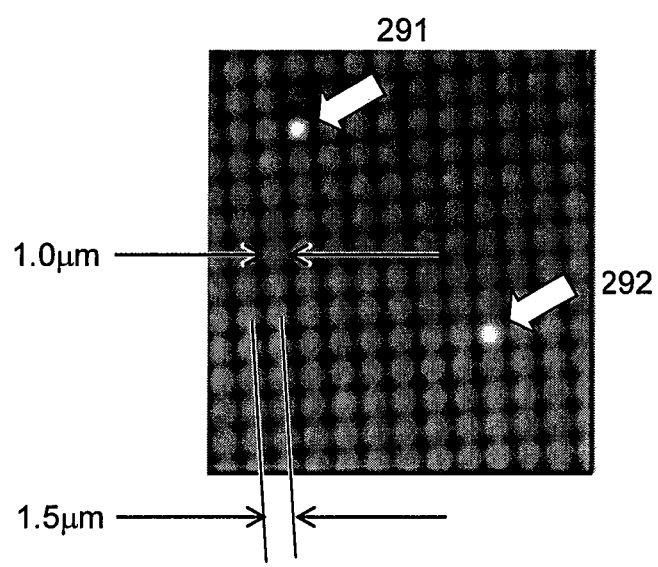
FIG. 12 shows the immobilization of concatemers on a substrate on which fine pillars have been formed.

FIG. 12 shows the results of labeling target concatemers (generated by the procedures described in Example 3) with a fluorescent moiety (PicoGreen, Invitrogen), immobilizing the concatemers on fine pillars, and then observing them by fluorescence microscopy. In FIG. 12, the diameter of each fine pillar is 1.0 µm, the height of each fine pillar is 1.0 µm, and the interval at which fine pillars are arranged is 1.5 µm.

As shown in FIG. 12, fluorescence 291 and fluorescence 292 are limited within certain ranges of the top faces of fine pillars.

Example 7

In this example, another method relating to the method for immobilizing the concatemer molecules 206 (produced by procedures based on the present invention) to be subjected to massively parallel nucleotide sequencing on the flow cell substrate 270 is exemplified.

Fine pillars 271 made of a resin material such as polystyrene are formed on the inner faces of flow paths of the flow cell substrate 270, which are made of glass. The fine pillars 271 are modified with an aminosilane molecule. The concatemers 206 containing DNA molecules are negatively charged, and thus can be electro-statistically bound to amino groups (FIGS. 11(a) and (b)).

As shown in FIG. 11(c), a solution 280 containing a reaction solution and others is applied to flow paths 273 and 272, so that sequence analysis can be conducted on concatemers 281, 282, and 283 immobilized on the top faces of fine pillars 274. Here, the height of each pillar is set to 0.5 μm or more, and the position of the focal point of an optical system for fluorescence detection is set on the top face of each pillar. Therefore, not only fluorescence from concatemers immobilized on the top faces, the sides, and the concave portions, such as 275, 276, and 277 via DNA immobilization treatment, but also from the concatemer 284 immobilized on the concave portion of the fine pillars 274, as in the case of 284, can be inhibited from mixing into the detection system.

Another example is a structure that inhibits the immobilization of concatemers on pillar concave portions by immobilizing the concatemers on only the top faces of the fine pillars 274 on a substrate on which the fine pillars 274 have been formed. The degree of hydrophilicity or hydrophobicity (repellency) of the surface of a fine pillar substrate including the top faces, the sides, and the concave portions can be controlled under conditions of oxygen plasma treatment, for example. The time for the above oxygen plasma treatment may be shortened, so that a state can be created wherein strong hydrophobicity is exhibited (such that the contact angle to water is 90° or more). When poly-L-lysine (Poly-L-Lysine: SIGMA-ALDRICH) is added dropwise to a fine pillar substrate in such a surface state, the poly-L-lysine solution comes into contact with only the pillar top faces without coming into contact with pillar concave portions and pillar sides. As shown in FIG. 11(d), poly-L-lysine adheres to only the top face as in the case of 285, and no poly-L-lysine adheres to a side 287 and a concave portion 286. Moreover, the side 287 and the concave portion 286 are hydrophobic and thus are not infiltrated with a solution 280 containing a probe and others, which is applied to a flow path in sequence analysis. Accordingly, concatemers 281, 282, and 283 as templates or probes do not reach faces other than top faces such as the top face of the fine pillar 285, and thus no reaction takes place on faces other than pillar top faces and detection accuracy can be improved.

Example 8

Figure 13:
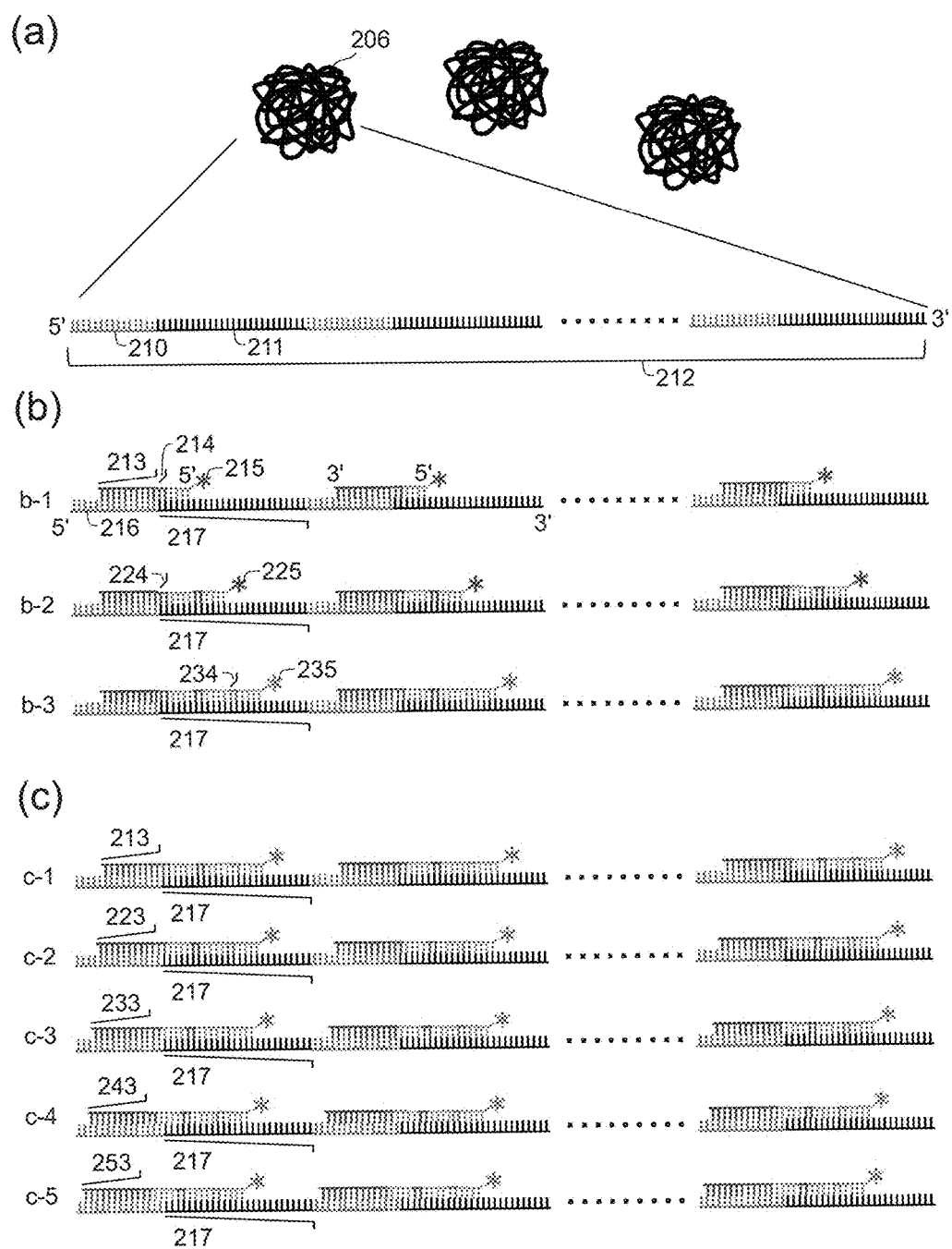
FIG. 13 shows examples of a method for determining the nucleotide sequence of a target DNA sequence using a product from the nucleic acid amplification reaction.

In this example, an example of a procedure of massively parallel nucleotide sequencing using concatemers produced by procedures based on the present invention is explained with reference to FIG. 13.

As an example of massively parallel nucleotide sequencing, sequence analysis based on ligation (sequencing by ligation) has been known (M. L. Metzker, "Sequencing technologies-the next generation", Nature Reviews Genetics Vol. 11, pages 31-46, 2010 (Non-patent Document 2)). A concatemer molecule 206 has a concatemer sequence 212, in which an adapter sequence 210 and a target DNA sequence 211 are linked in series, as shown in FIG. 13(a).

As shown in FIG. 13(b), a primer 213 binds to the primer recognition site in an adapter DNA sequence 216, and then a probe (first nucleotide recognition site) 214 that recognizes a sequence of 2-nucleotide on the 5' side of the primer 213 is ligated. The probe has been modified with a dye (first label) 215 corresponding to the 2-nucleotide sequence. The fluorescence signal of the dye is read, so as to allow the 2-nucleotide sequence that is a target DNA sequence 217 to be known (b-1 in FIG. 13(b)). Next, after 215 is removed, two nucleotides on the 5' end of a probe (containing a second nucleotide recognition site 224) that has been modified with a dye (second label) 225 are read (b-2 in FIG. 13(b)). Two nucleotides subsequent thereto are read by a similar reaction using 234 and 235 (b-3 in FIG. 13(b)). This is repeated sequentially to analyze the sequence from the primer end.

A probe to be used herein is prepared so as to have a nucleotide length that allows improvement of hybridization stability through the addition of 6 nucleotides to a sequence recognition site of 2-nucleotide. Hence, as shown in FIG. 13(c), a plurality of primers 213, 223, 233, 243, and 253 are prepared, so that hybridization to recognition sites that may vary by nucleotide can take place sequentially. All of the regions of the target DNA sequence 217 can be read by shifting the position for the initiation of ligation.

Concatemers 212 have many primer recognition sites in series in an adapter DNA sequence 210, so that a plurality of similar ligation reactions proceed simultaneously within one concatemer. Strong signal strength can be obtained corresponding to the number of adapter-to-target DNA sequence ligations linked in series.

In addition, the present invention is not limited to the above examples and can include various modifications and changes. For example, the above examples are described in detail for simple explanation of the present invention. The present invention is not always limited to the one comprising all the elements explained herein. Furthermore, a portion of the element(s) of an example can be substituted with the element(s) of another example, and the element(s) of another example can also be added to the element(s) of an example. Moreover, another element(s) can be added to, deleted from, or substituted with a portion of the element(s) of any example.

DESCRIPTION OF SYMBOLS

1: Target DNA fragment
2: DNA fragment complementary to 1
3: DNA sequence composing adapter
4: DNA sequence composing adapter
5: Nick
6: DNA sequence capable of forming folded structure with 3
7: DNA sequence complementary to 3
8: DNA sequence complementary to 4
9: DNA sequence complementary to 6
10: Portion of adapter elongated with DNA sequence 7 as template
11: Portion of adapter elongated with DNA sequence 8 as template 12: Portion of adapter elongated with DNA sequence 9 as template
13: Portion of adapter elongated with DNA sequence 7 as template
14: Portion of adapter elongated with DNA sequence 8 as template
15: Portion of adapter elongated with DNA sequence 9 as template
16: Portion of adapter elongated with DNA sequence 9 as template
17: Target DNA fragment elongated with DNA fragment 2 as template
18: Target DNA fragment elongated with DNA fragment 2 as template
20: Double-stranded adapter
21: Double-stranded adapter
29: Concatemer
101: Target DNA fragment
102: DNA fragment complementary to 101
103: DNA sequence composing adapter
104: DNA sequence composing adapter
105: Nick
106: DNA sequence capable of forming folded structure with 103
107: DNA sequence complementary to 103
108: DNA sequence complementary to 104
109: DNA sequence complementary to 106
110: Portion of adapter elongated with DNA sequence 107 as template
111: Portion of adapter elongated with DNA sequence 108 as template
112: Portion of adapter elongated with DNA sequence 109 as template
113: Portion of adapter elongated with DNA sequence 106 as template
114: Portion of adapter elongated with DNA sequence 104 as template
115: Portion of adapter elongated with DNA sequence 103 as template
116: Portion of DNA sequence complementary to target DNA fragment 101 elongated with DNA fragment 101 as template
117: DNA sequence having the same sequence as that of target DNA fragment elongated with DNA sequence 116 as template
118: Portion of adapter elongated with DNA sequence 112 as template
119: Portion of adapter elongated with DNA sequence 111 as template
120: Portion of adapter elongated with DNA sequence 110 as template
121: Portion of DNA sequence complementary to target DNA fragment 101 elongated with DNA fragment 101 as template
122: Portion of adapter elongated with DNA sequence 106 as template
123: Portion of adapter elongated with DNA sequence 104 as template
124: Portion of adapter elongated with DNA sequence 103 as template
129: Concatemer
130: DNA sequence containing recognition site of primer
131: DNA sequence containing recognition site of primer
132: Sequence forming cohesive end
133: Sequence forming cohesive end
134: Restriction enzyme recognition sequence
135: Restriction enzyme recognition sequence
136: Primer sequence comprising: a DNA sequence containing a recognition site of primer; a sequence forming a cohesive end; and a restriction enzyme recognition sequence
137: Primer sequence comprising: a DNA sequence containing a recognition site of primer; a sequence forming a cohesive end; and a restriction enzyme recognition sequence
138: Sequence complementary to 136
139: Sequence complementary to 137
140: DNA sequence complementary to DNA sequence 130
141: DNA sequence complementary to DNA sequence 131
150: Restriction enzyme cleavage site
151: Restriction enzyme cleavage site
152: Double-stranded DNA fragment to be analyzed
155: Nick
201: Genomic DNA
202: Fragmented genomic DNA
203, 203a, 203b, 203c, 203d, 203e, 203f: Target DNA sequences in template DNA
204: Adapter sequence in template DNA
205: Template DNA
206, 206a, 206b, 206c, 206d, 206e, 206f: Concatemers in the form of DNA nanoballs
207: Flow path substrate
208: Area affected by the electrostatic force of concatemer/amino group
209: Flow cell substrate
210: Adapter DNA sequence
211: Target DNA sequence
212: Concatemer sequence
213: Primer/primer of first primer round
214: First nucleotide recognition site
215: First label
216: Adapter DNA sequence
217: Target DNA sequence
223: Primer of second primer round
224: Second nucleotide recognition site
225: Second label
233: Primer of third primer round
234: Third nucleotide recognition site
235: Third label
243: Primer of fourth primer round
253: Primer of fifth primer round
270: Flow cell substrate (flow path substrate)
271: Fine pillar
272: Structure composing the bottom face of flow cell substrate (flow path substrate)
273: Structure composing the top face of flow cell substrate (flow path substrate)
274: Fine pillar
275: Top face of fine pillar subjected to DNA immobilization treatment
276: Portion (concave) with no flow cell, which is the bottom face of flow cell substrate (flow path substrate) subjected to DNA immobilization treatment
277: Side of fine pillar subjected to DNA immobilization treatment
280: Reaction solution
281: Concatemer immobilized on the top face of fine pillar
282: Concatemer immobilized on the top face of fine pillar
283: Concatemer immobilized on the top face of fine pillar 284: Concatemer immobilized on the bottom face of flow cell substrate (flow path substrate) with no fine pillar
285: Top face of fine pillar subjected to DNA immobilization treatment
286: Portion (concave) with no flow cell, which is the bottom face of flow cell substrate (flow path substrate) not subjected to DNA immobilization treatment
287: Side of fine pillar not subjected to DNA immobilization treatment
291: Fluorescence of concatemer immobilized on fine pillar
292: Fluorescence of concatemer immobilized on fine pillar

SEQUENCE LISTING FREE TEXT

SEQ ID NOS: 1-8: Artificial sequence (synthetic DNA)
All publications, patents, and patent applications cited herein are incorporated herein by reference in their entirety.

The invention claimed is:

1. A method for amplifying a nucleic acid, comprising the steps of:
   (a) ligating a double-stranded adapter that contains adapter DNA strands capable of forming a folded structure to a double-stranded DNA that contains a target DNA sequence to prepare a cyclic DNA template composed of nick-containing double-stranded DNA; and
   (b) performing a 3' end elongation reaction from the nick as an origin using a strand-displacement DNA polymerase, thereby producing a concatemer in which a plurality of the target DNA sequences and the adapter DNA strands capable of forming the folded structure are linked in series as a single-stranded DNA, wherein no primers other than said adapter are used in the method,
   wherein the concatemer has a folded shape due to the folded structure, and
   wherein the double-stranded adapter has an adapter DNA strand that has a first DNA sequence, a second DNA sequence, and a third DNA sequence, wherein the first and the third DNA sequences are capable of forming a folded structure, and the adapter DNA strand and an adapter DNA strand complementary thereto are bound to form a double-strand.

2. The method according to claim 1, wherein the double-stranded adapter has from the 5' end to the 3' end: an adapter DNA strand composed of the first DNA sequence, the second DNA sequence, and the third DNA sequence in this order; an adapter DNA strand composed of the first DNA sequence, the third DNA sequence, and the second DNA sequence in this order; or an adapter DNA strand composed of the second DNA sequence, the first DNA sequence, and the third DNA sequence in this order.

3. The method according to claim 1, wherein
   the double-stranded adapter contains a first adapter DNA strand and a second adapter DNA strand complementary to the first adapter DNA strand, and the first adapter DNA strand and the second adapter DNA strand are bound to form a double-strand;
   the first adapter DNA strand has, from the 5' end to the 3' end, a first DNA sequence, a second DNA sequence, and a third DNA sequence, and the first and the third DNA sequences are capable of forming a folded structure;
   the second adapter DNA strand has, from the 5' end to the 3' end, a third complementary sequence complementary to the third DNA sequence, a second complementary sequence complementary to the second DNA sequence, and a first complementary sequence complementary to the first DNA sequence, and the first and the third complementary sequences are capable of forming a folded structure; and
   the method comprises the steps of:
   (b1) generating, in the cyclic DNA template, a first nick at the 5' end of the first DNA sequence on the first adapter DNA strand, and generating a second nick at the 5' end of the third complementary sequence on the second adapter DNA strand,
   (b2) performing a 3' end elongation reaction from the first nick as an origin to the position of the second nick on the second adapter DNA strand using a strand-displacement DNA polymerase to generate an adapter DNA strand having the same sequence as that of the first adapter DNA strand and stop the elongation reaction, and thereby forming a folded structure by the adapter DNA strands,
   (b3) performing a 3' end elongation reaction of the adapter DNA strands to elongate a DNA sequence complementary to the target DNA sequence, and next generate an adapter DNA strand having the same sequence as that of the second adapter DNA strand, and thereby forming a folded structure by the adapter DNA strands,
   (b4) performing a 3' end elongation reaction of the adapter DNA strands to elongate the same DNA sequence as that of the target DNA sequence, and next generate an adapter DNA strand having the same sequence as that of the first adapter DNA strand, and thereby forming a folded structure by the adapter DNA strands, and (b5) reating steps (b3) and (b4), such that a concatemer is produced, in which a plurality of the target DNA sequences, the first adapter DNA strands, the DNA sequences complementary to the target DNA sequences, and the second adapter DNA strands are linked in series.

4. A method for determining a nucleotide sequence, comprising the steps of:

immobilizing one or a plurality of concatemers produced by the method according to any one of claims 2, or 3 on a flow path substrate;

binding a primer to a sequence other than sequences capable of forming a folded structure of the adapter DNA strands in each concatemer;

sequentially ligating a probe that contains a recognition site consisting of a plurality of nucleotides and is bound with a label corresponding to the nucleotide type of the recognition site to an end of the primer; and detecting the ligated probe based on the label to determine the nucleotide sequence of the target DNA sequence.

5. The method according to claim 1, wherein the double-stranded adapter contains a first adapter DNA strand and a second adapter DNA strand complementary to the first adapter DNA, and both the first adapter DNA strand and the second adapter DNA strand have a sequence that contain a nick or is capable of generating a nick.

* * * * *